United States Patent [19]

Gordon et al.

[11] Patent Number: 5,741,279
[45] Date of Patent: Apr. 21, 1998

[54] ENDOSCOPIC SUTURE SYSTEM

[75] Inventors: Norman S. Gordon, Irvine, Calif.;
Robert P. Cooper, Yorba Linda, Calif.

[73] Assignee: Laurus Medical Corporation, Irvine, Calif.

[21] Appl. No.: 743,886

[22] Filed: Nov. 6, 1996

Related U.S. Application Data

[60] Division of Ser. No. 311,967, Sep. 26, 1994, Pat. No. 5,578,044, which is a continuation-in-part of Ser. No. 205,042, Mar. 2, 1994, Pat. No. 5,540,704, which is a continuation-in-part of Ser. No. 57,699, May 4, 1993, Pat. No. 5,458,609, which is a continuation-in-part of Ser. No. 941,382, Sep. 4, 1992, Pat. No. 5,364,408.

[51] Int. Cl.[6] .................................................. A61B 17/04
[52] U.S. Cl. .................. 606/144; 606/139; 606/145; 606/148; 606/223; 216/56
[58] Field of Search ............................ 216/56; 606/139, 606/144, 145, 148, 222–227

[56] References Cited

U.S. PATENT DOCUMENTS

| | | |
|---|---|---|
| 342,773 | 6/1886 | Bailey . |
| 919,138 | 4/1909 | Drake et al. . |
| 1,037,864 | 9/1912 | Carlson et al. . |
| 1,449,087 | 3/1923 | Bugbee . |
| 1,815,725 | 7/1931 | Pilling et al. . |
| 1,822,330 | 9/1931 | Ainslie . |
| 2,577,240 | 12/1951 | Findley . |
| 2,579,192 | 12/1951 | Kohl . |
| 3,013,559 | 12/1961 | Thomas . |
| 3,160,157 | 12/1964 | Chisman . |
| 3,470,875 | 10/1969 | Johnson . |
| 3,638,653 | 2/1972 | Berry . |
| 3,840,017 | 10/1974 | Violante . |
| 3,918,455 | 11/1975 | Coplan . |
| 3,946,740 | 3/1976 | Bassett . |
| 4,161,951 | 7/1979 | Scanlan, Jr. . |
| 4,164,225 | 8/1979 | Johnson et al. . |
| 4,224,947 | 9/1980 | Fukuda . |
| 4,235,177 | 11/1980 | Arbucklie . |
| 4,236,470 | 12/1980 | Stenson . |
| 4,312,337 | 1/1982 | Donohue . |
| 4,345,601 | 8/1982 | Fukuda . |
| 4,493,323 | 1/1985 | Albright et al. . |
| 4,548,202 | 10/1985 | Duncan . |
| 4,557,265 | 12/1985 | Andersson . |
| 4,596,249 | 6/1986 | Freda et al. . |
| 4,602,635 | 7/1986 | Mulhollan et al. . |
| 4,621,640 | 11/1986 | Mulhollan et al. . |
| 4,635,638 | 1/1987 | Weintraub et al. . |
| 4,762,260 | 8/1988 | Richards et al. ................ 227/19 |
| 4,781,190 | 11/1988 | Lee . |
| 4,890,615 | 1/1990 | Caspari et al. . |
| 4,898,155 | 2/1990 | Ovil et al. . |
| 4,899,746 | 2/1990 | Brunk . |
| 4,923,461 | 5/1990 | Caspari et al. . |
| 4,926,860 | 5/1990 | Stice et al. . |
| 4,935,027 | 6/1990 | Yoon . |
| 4,957,498 | 9/1990 | Caspari et al. . |
| 5,037,433 | 8/1991 | Wilk et al. . |
| 5,047,039 | 9/1991 | Avant et al. . |
| 5,067,957 | 11/1991 | Jervis . |
| 5,100,415 | 3/1992 | Hayhurst . |
| 5,100,418 | 3/1992 | Yoon et al. . |
| 5,100,421 | 3/1992 | Christoudias . |
| 5,100,498 | 3/1992 | Takeuchi et al. ................ 156/634 |
| 5,188,636 | 2/1993 | Fedotov . |
| 5,258,011 | 11/1993 | Drews . |
| 5,306,281 | 4/1994 | Beurrier . |
| 5,308,353 | 5/1994 | Beurrier . |
| 5,387,221 | 2/1995 | Bisgaard . |
| 5,389,103 | 2/1995 | Melzer et al. . |
| 5,391,174 | 2/1995 | Weston . |
| 5,417,699 | 5/1995 | Klein et al. . |
| 5,527,321 | 6/1996 | Hinchliffe . |

FOREIGN PATENT DOCUMENTS

| | | |
|---|---|---|
| 647813 | 9/1962 | Canada . |
| 0 140 557 | 5/1985 | European Pat. Off. . |
| 0 589 409 | 3/1994 | European Pat. Off. . |
| 1028320 | 6/1983 | U.S.S.R. . |
| 1093329 | 5/1984 | U.S.S.R. . |
| WO/90/03766 | 4/1990 | U.S.S.R. . |
| 18 602 | 9/1909 | United Kingdom . |
| 2 247 841 | 3/1992 | United Kingdom . |
| WO/92/12674 | 8/1992 | WIPO . |
| WO/93/01750 | 2/1993 | WIPO . |
| WO/94/13211 | 6/1994 | WIPO . |

OTHER PUBLICATIONS

Description of "Rema Deep Suture", publication status and dates unknown, original document in German, English translation attached.

*Primary Examiner*—Gary Jackson
*Attorney, Agent, or Firm*—Dennis H. Epperson

[57] ABSTRACT

A method and device for the placement of sutures and for the purpose of approximating tissue. A particular utility is effected in the approximation of the tissue separated by means of an endosurgical trocar being inserted into a body cavity. The invention provides for the loading of suture material including needles into the device, introduction and placement of the device into the body cavity, with the distal end having deployable needle guides, extending the needle guides either simultaneously or individually to the periphery of the wound, engaging the wound with the needle guides, driving the needles and suture material through the tissue to be approximated into a catch mechanism, retracting the needle guides and withdrawing the device, leaving a loop of suture material in the margin of tissue. The suture may then be tied to approximate the wound and excess suture material cut off. The invention also provides for the placement of sutures for the endoscopic approximation, fixation, and ligation of tissues within a body cavity including the driving and retrieval of needle and suture combinations, and facilitating the tying of knots.

10 Claims, 16 Drawing Sheets

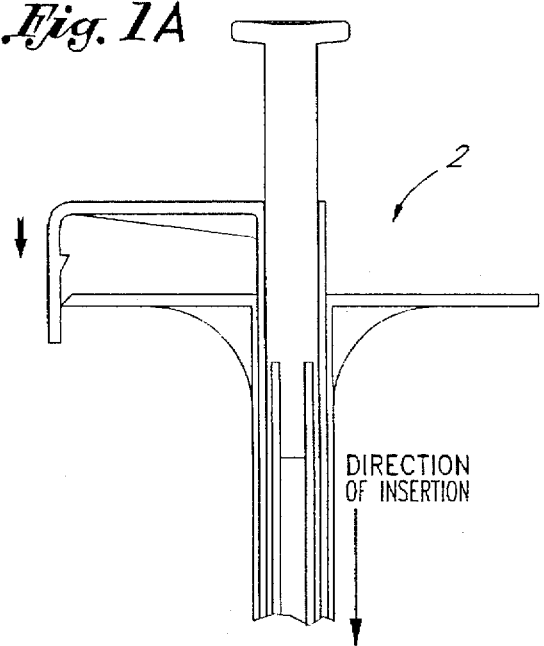
Fig. 1A
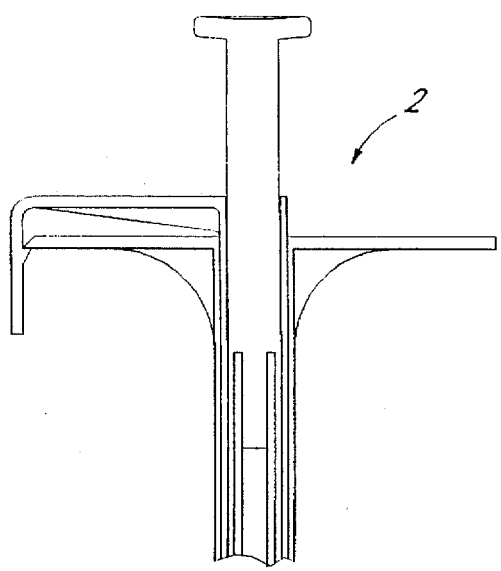
Fig. 1B
DIRECTION OF INSERTION
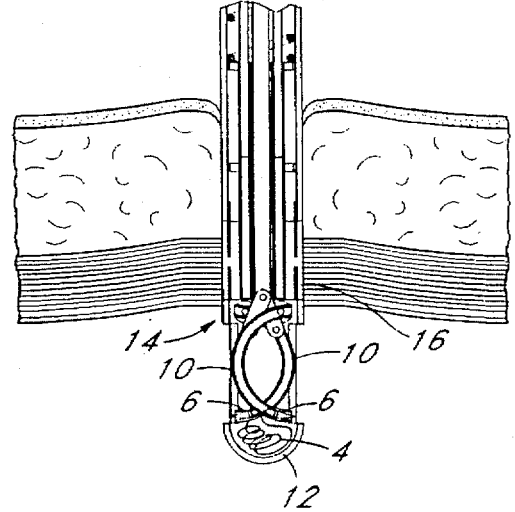
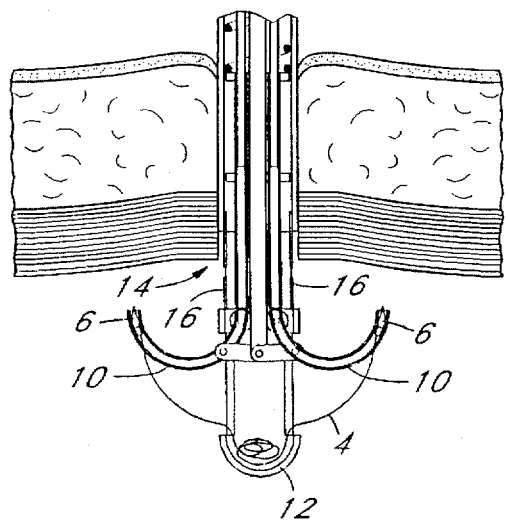

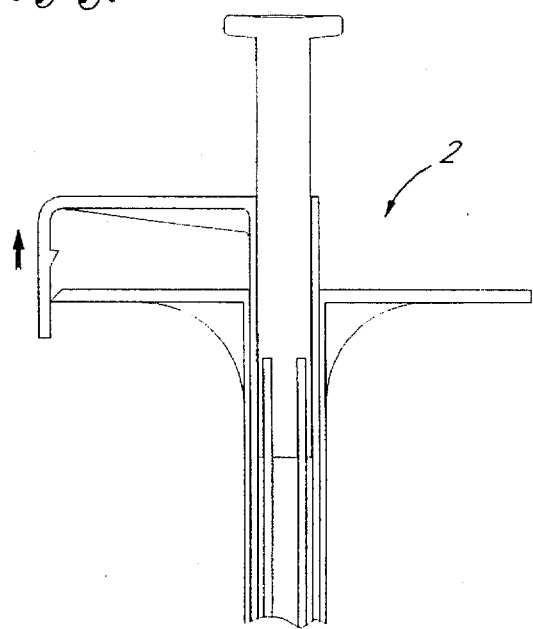
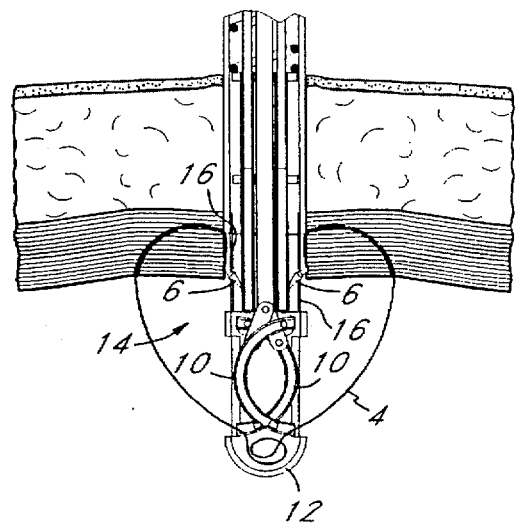
Fig. 1G
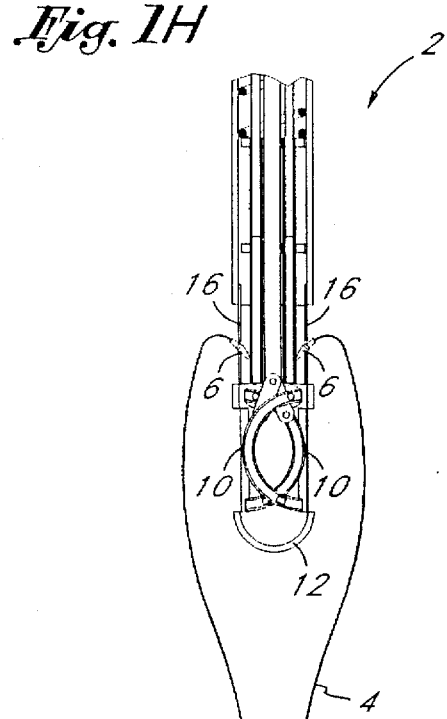
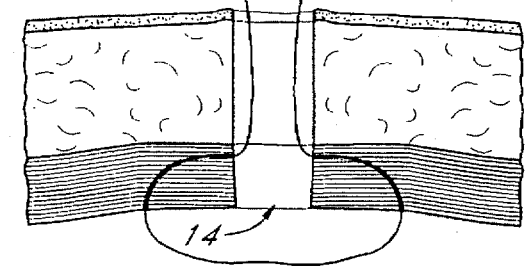
Fig. 1H

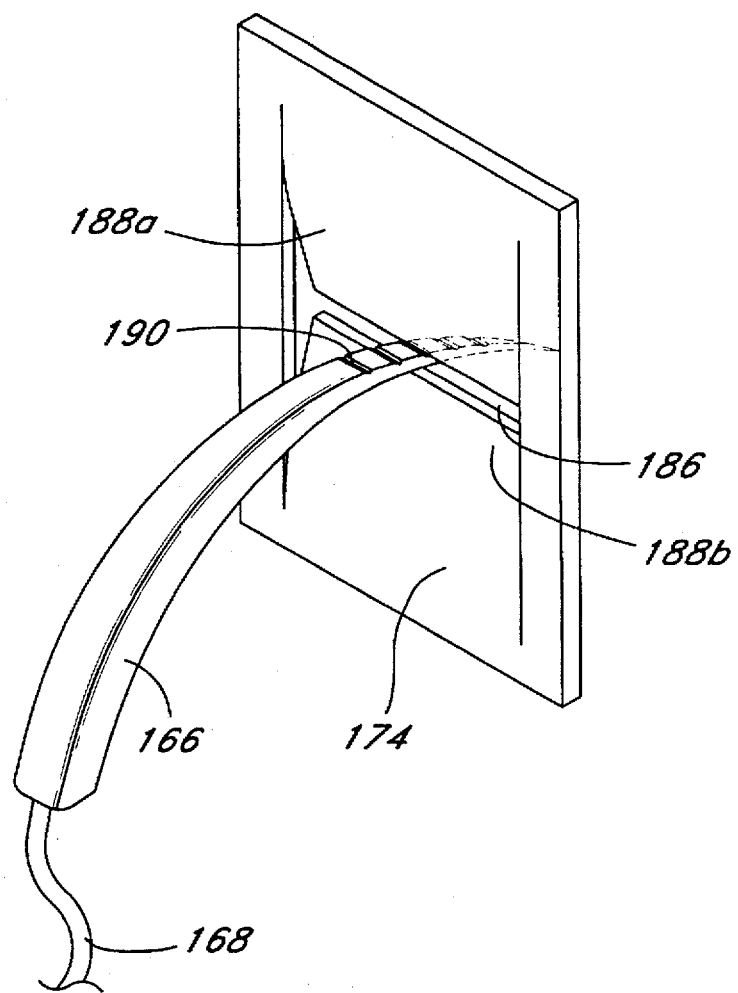

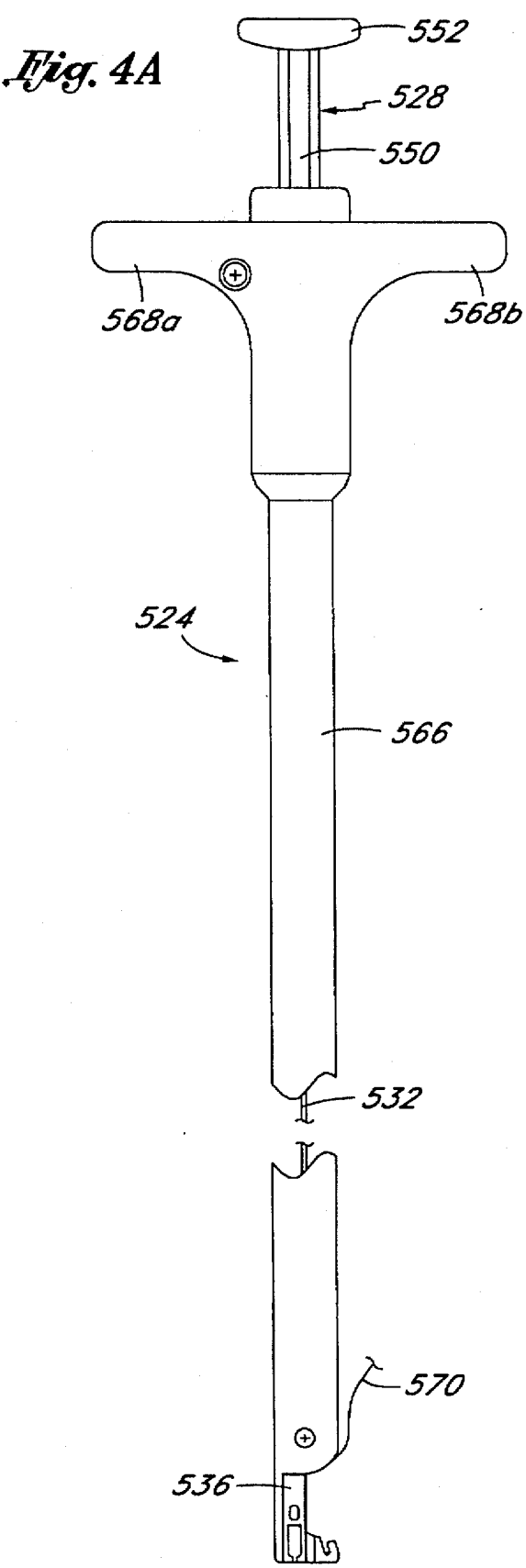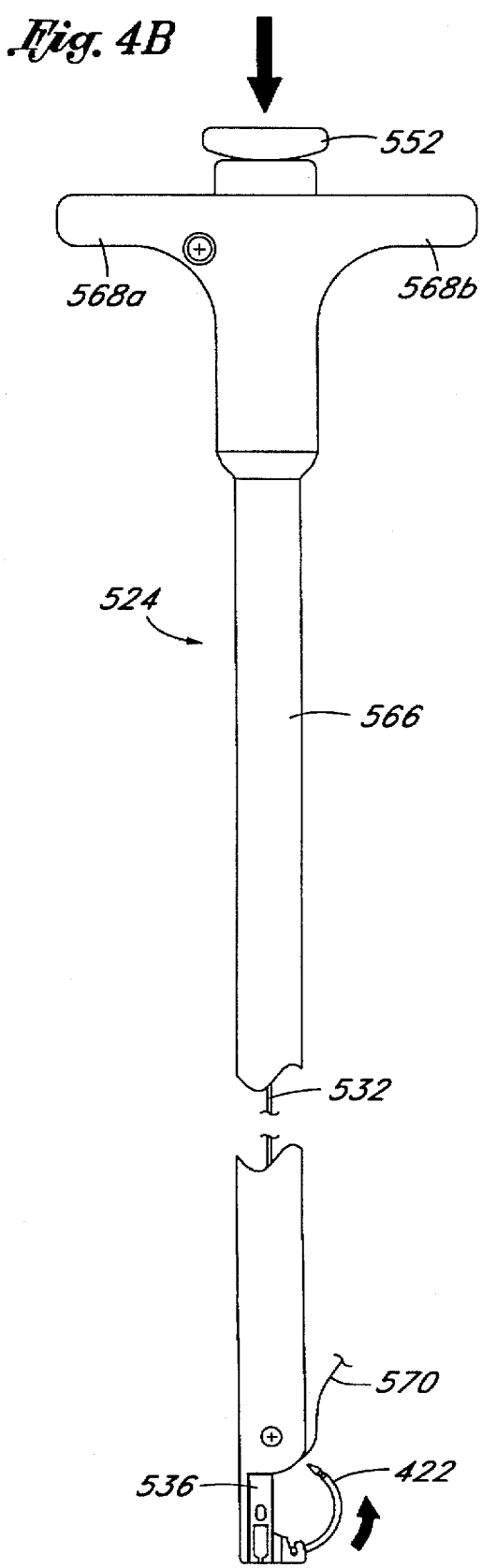

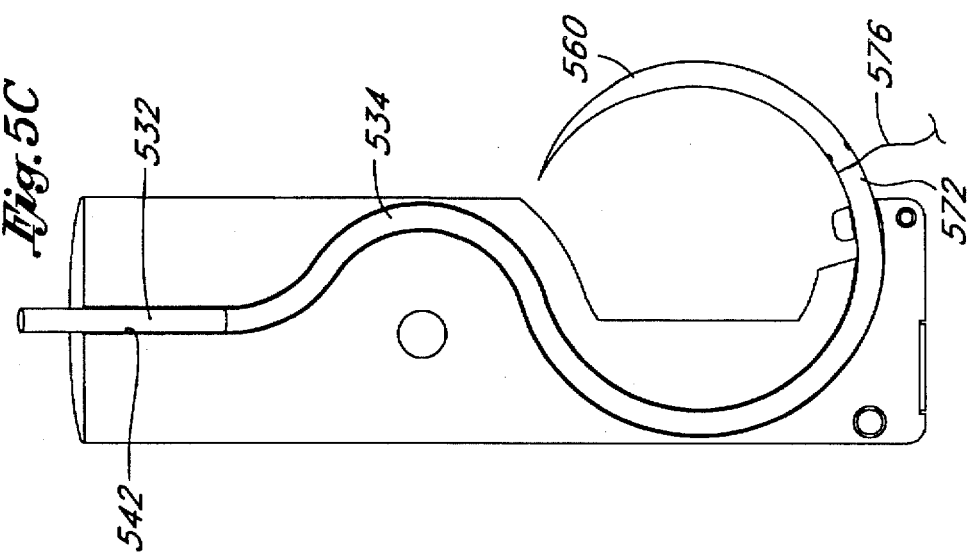
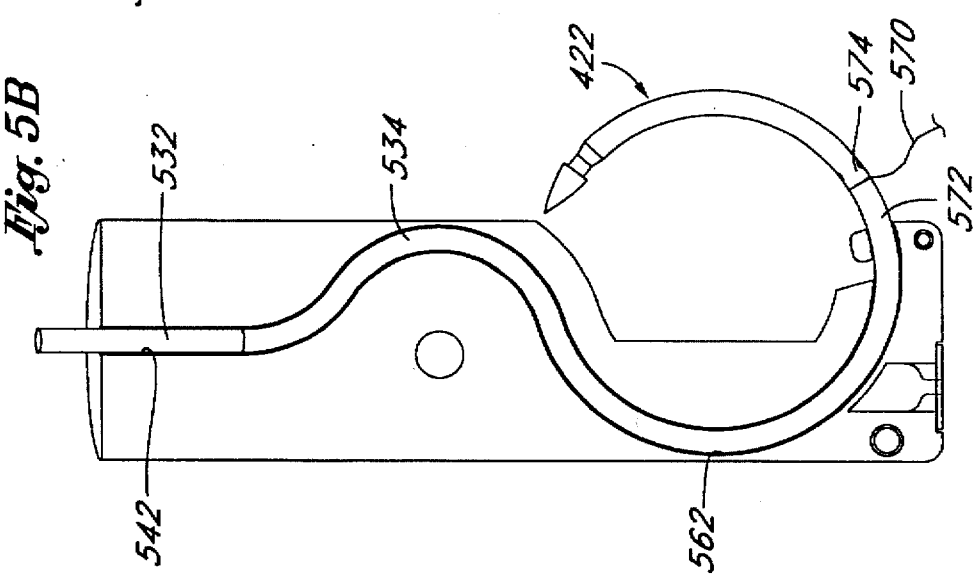
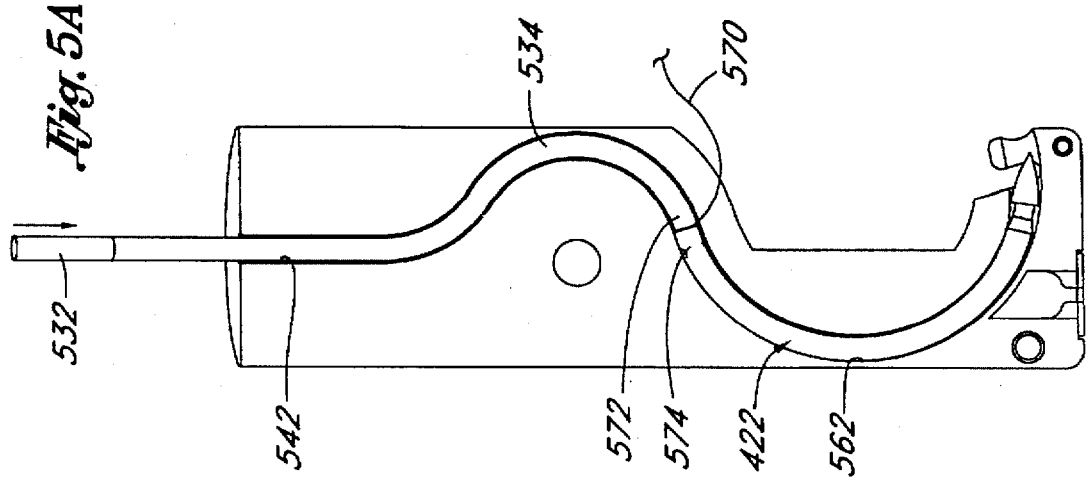

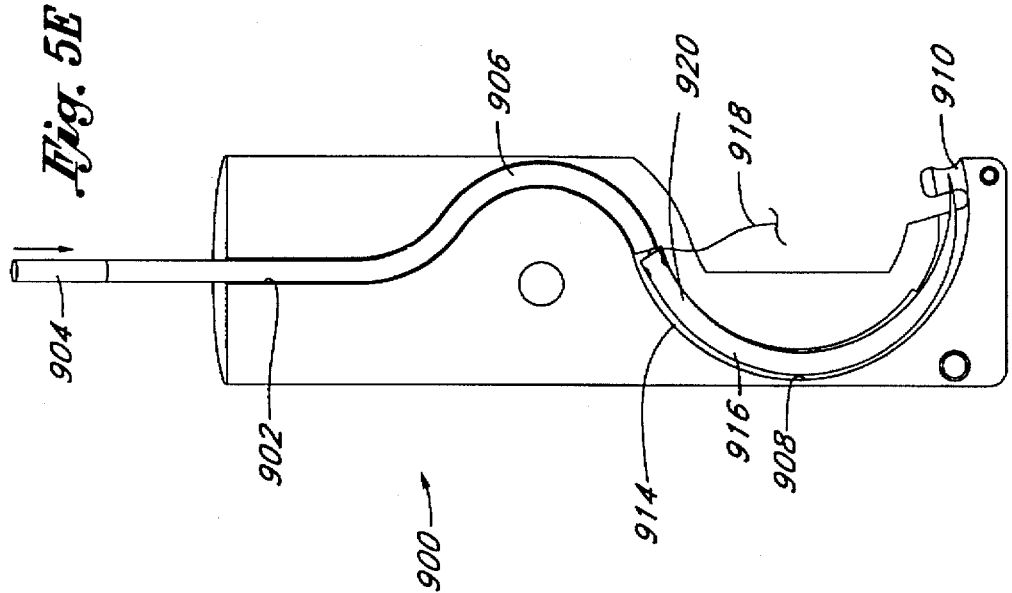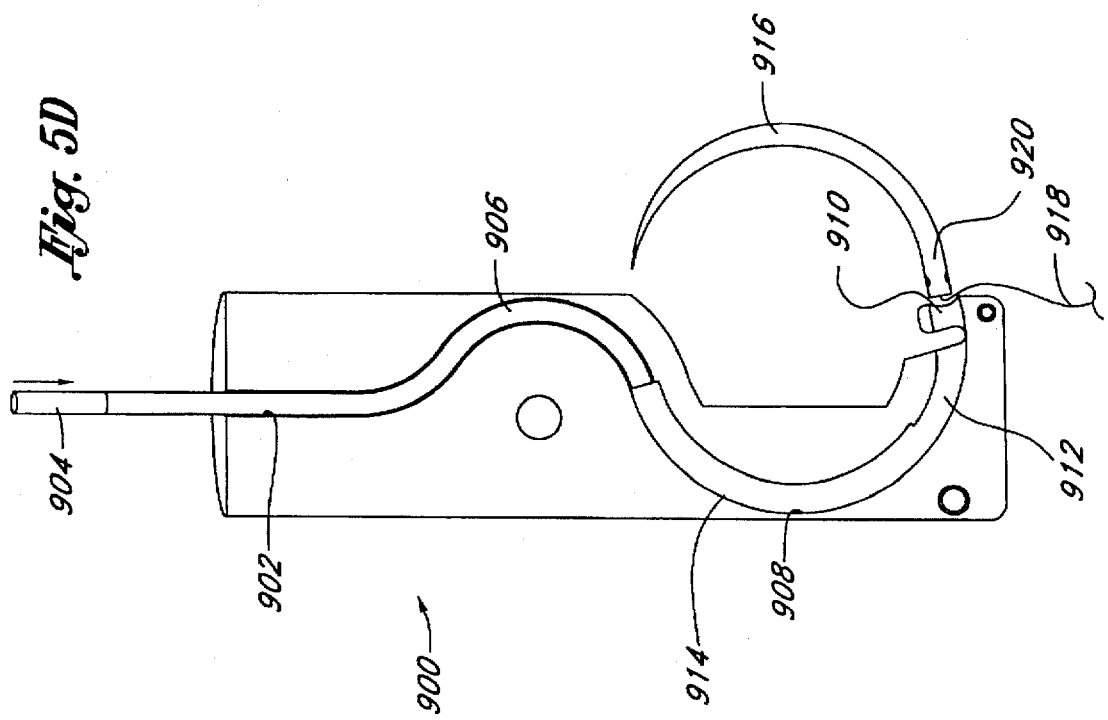

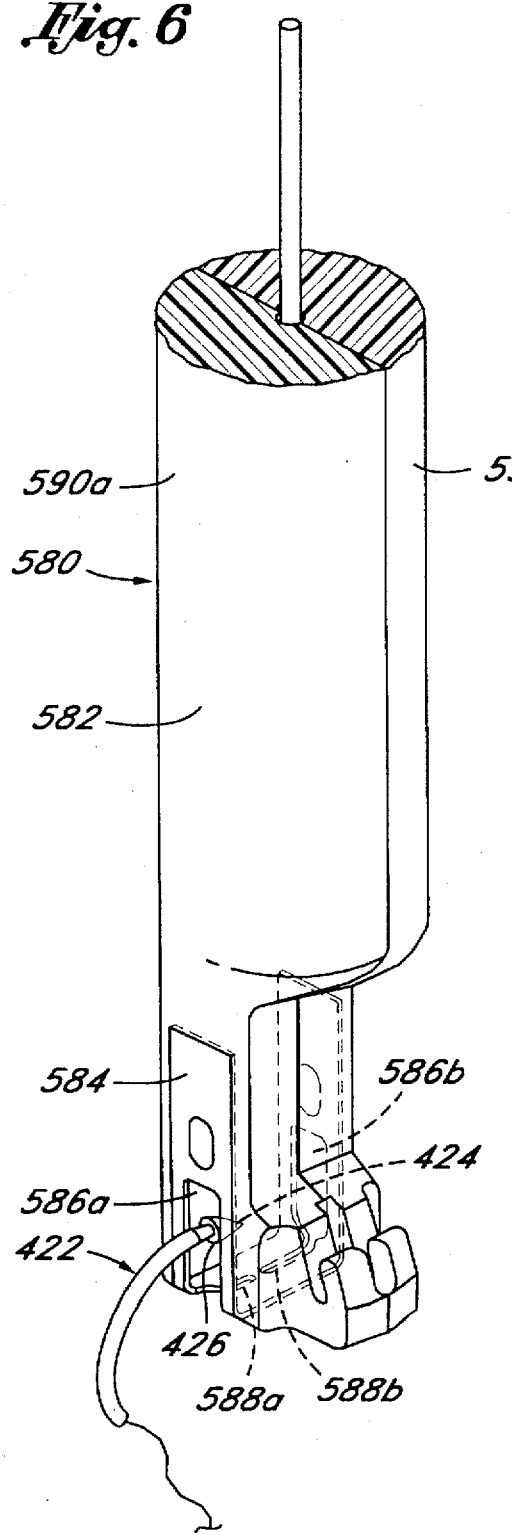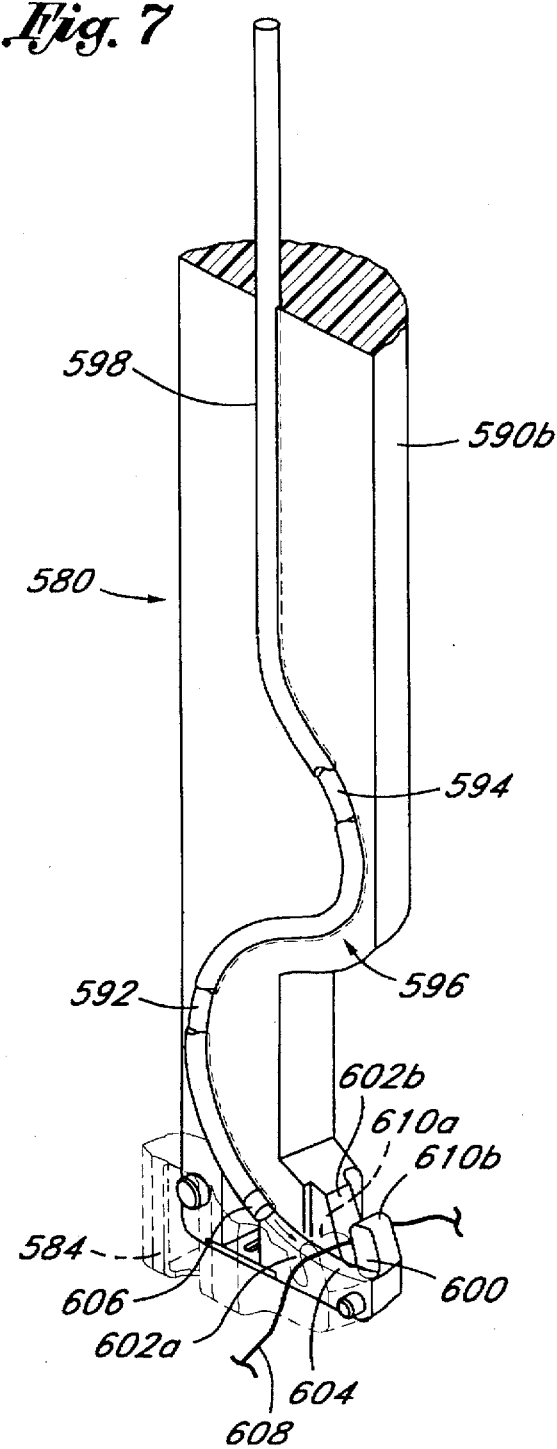

Fig. 8
Fig. 8A
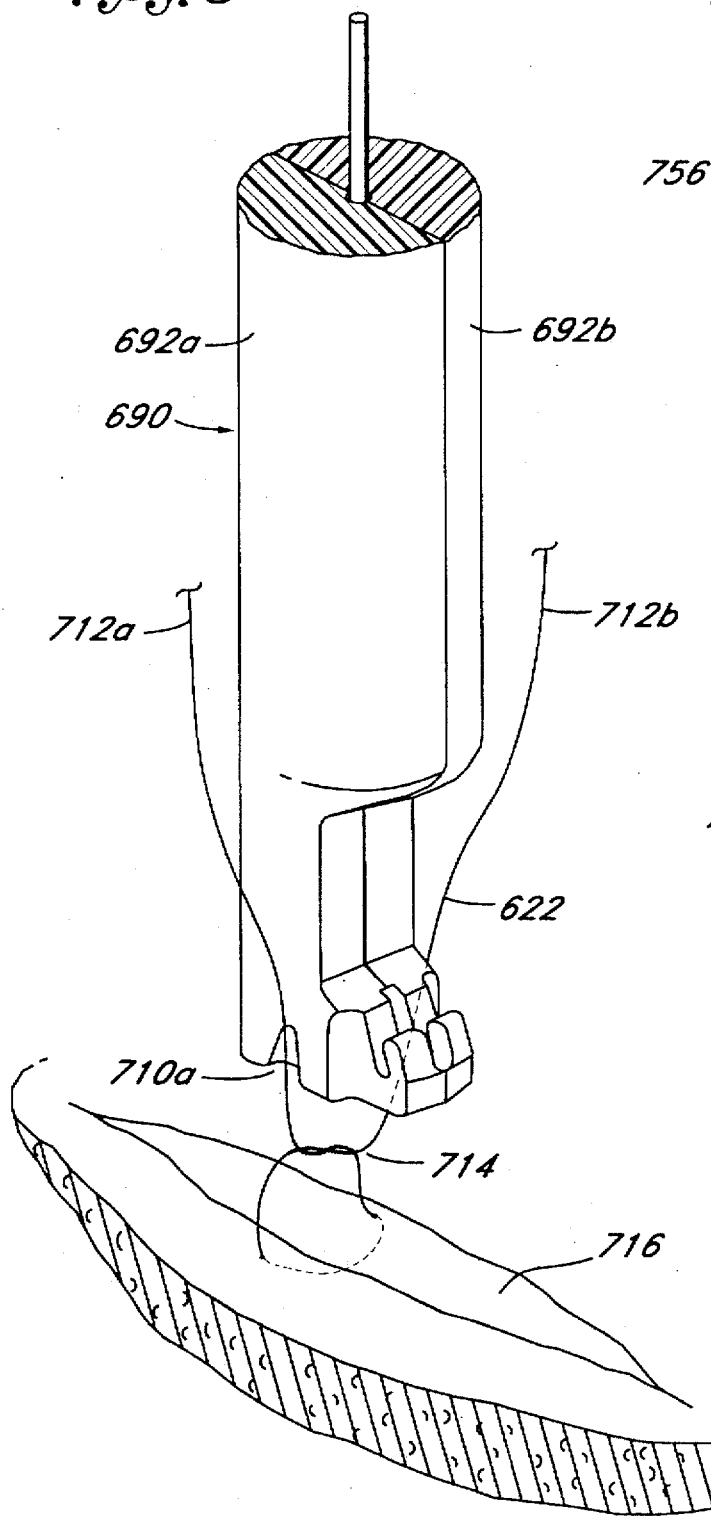
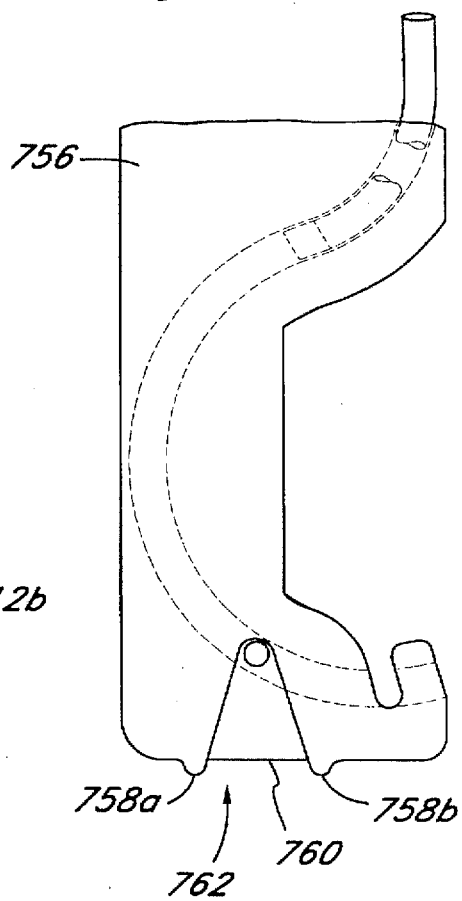

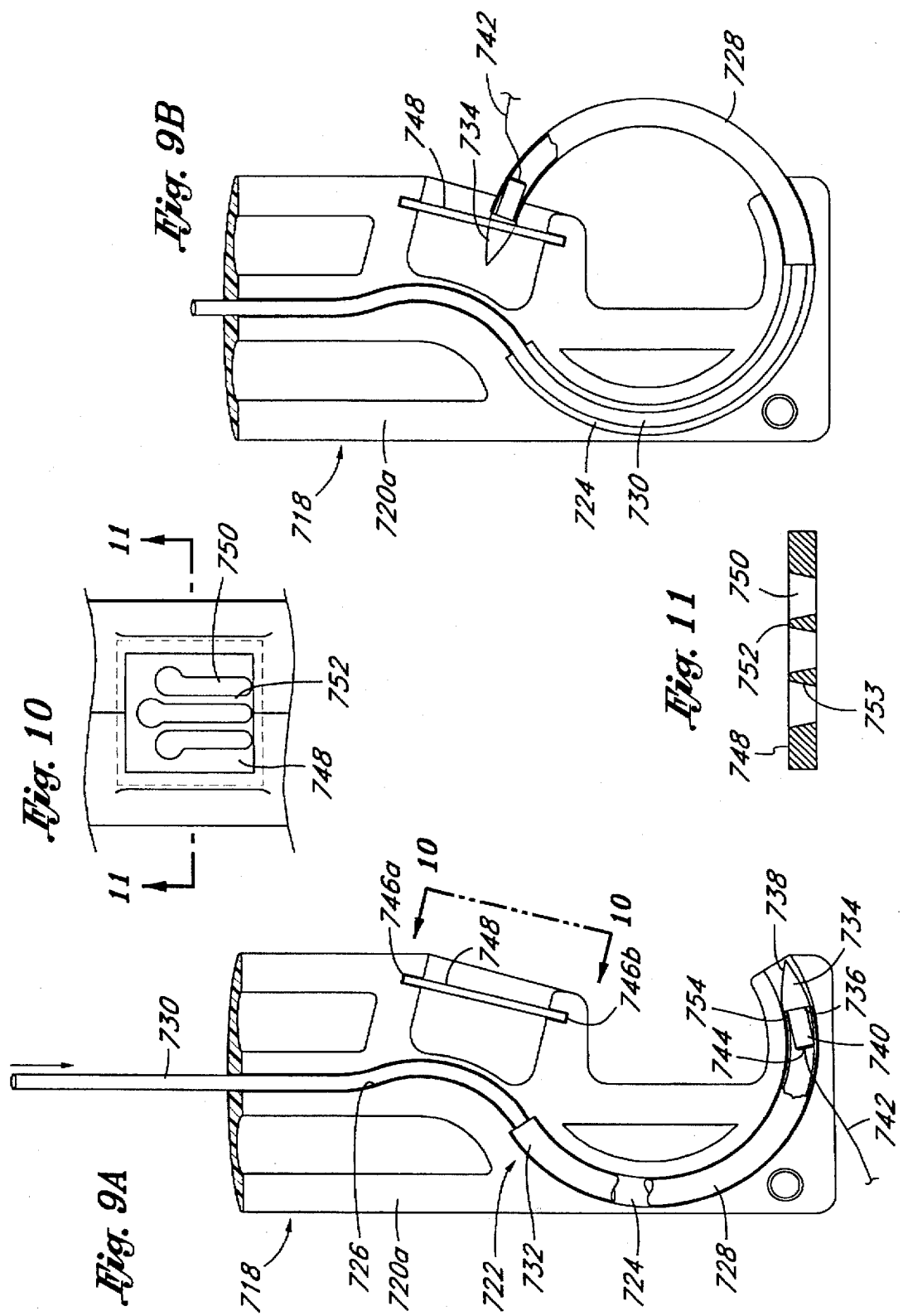

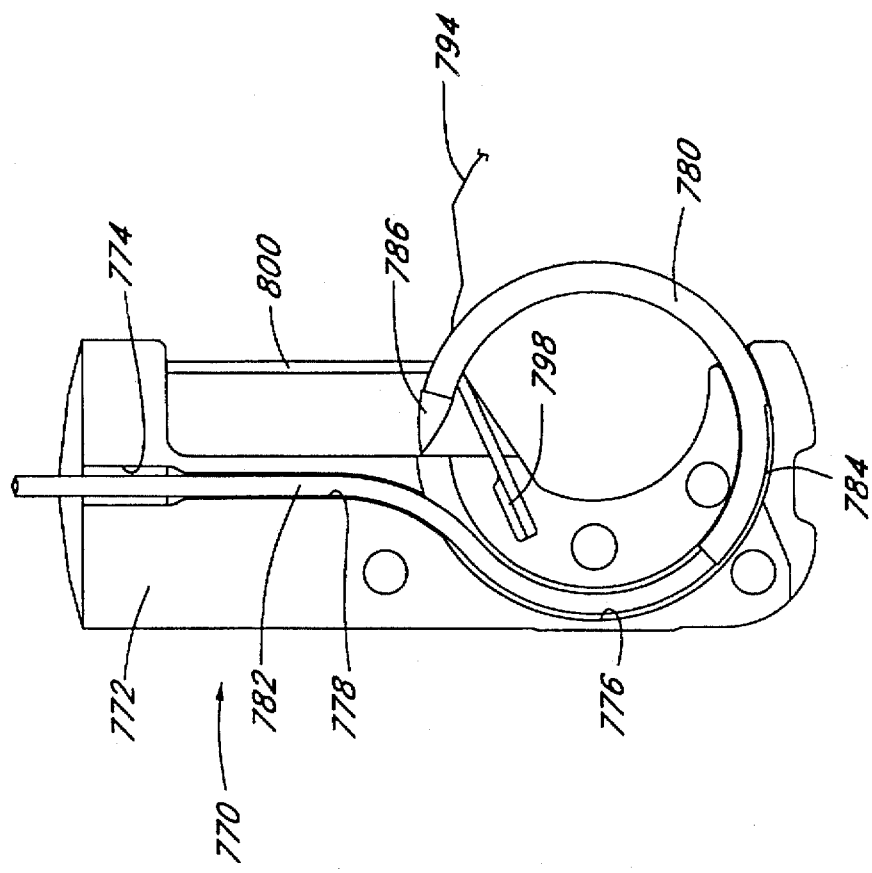
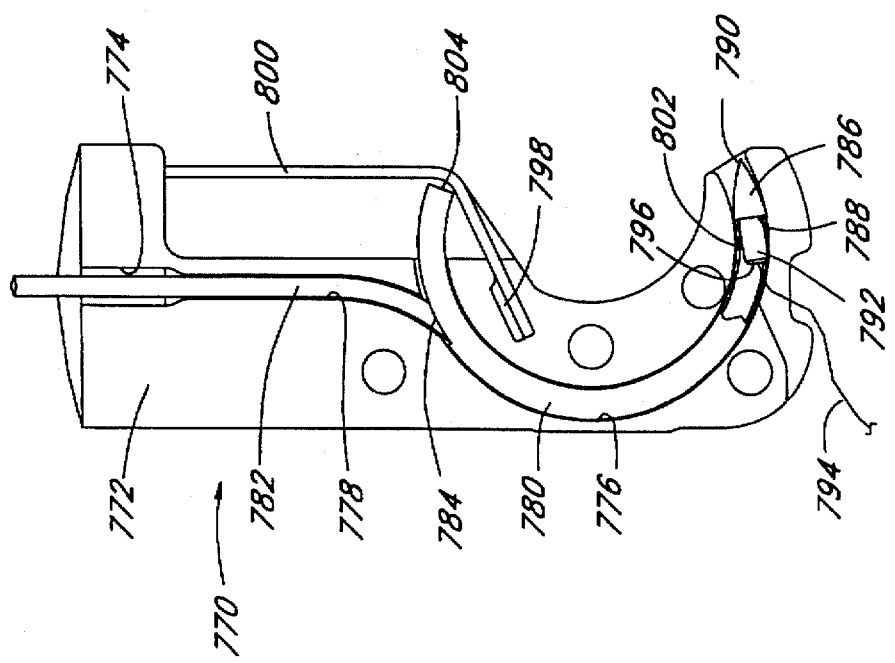

ENDOSCOPIC SUTURE SYSTEM

RELATED APPLICATIONS

This patent application is a division of application Ser. No. 08/311,967; filed on Sep. 26, 1994, now U.S. Pat. No. 5,578,044, which is a continuation-in-part of patent application Ser. No. 08/205,042, filed Mar. 2, 1994, now U.S. Pat. No. 5,540,704 by inventors Norman S. Gordon, Robert P. Cooper and Gordon C. Gunn, and entitled "Endoscopic Suture System", which is a continuation-in-part of patent application Ser. No. 08/057,699, filed May 4, 1993 now U.S. Pat. No. 5,458,609, by inventors Norman S. Gordon, Robert P. Cooper and Richard L. Quick, and entitled "Endoscopic Suture System" which is a continuation-in-part of patent application Ser. No. 07/941,382, filed Sep. 4, 1992, now U.S. Pat. No. 5,364,408 by inventor Norman S. Gordon, and entitled "Endoscopic Suture System". The entirety of each of the above referenced patent applications is hereby incorporated herein by reference.

FIELD OF THE INVENTION

The invention relates to devices for approximation, ligation and fixation of tissue using a suture, and particularly to the tissue separated by means of an endosurgical trocar being inserted into a body cavity, and to approximation, ligation, and fixation of tissue using endosurgical techniques.

BACKGROUND OF THE INVENTION

Suturing of body tissues is a time consuming aspect of most surgical procedures. Many surgical procedures are currently being performed where it is necessary to make a large opening to expose the area of, for instance, the human body that requires surgical repair. There are instruments that are becoming increasingly available that allow the viewing of certain areas of the body through a small puncture wound without exposing the entire body cavity. These viewing instruments, called endoscopes, can be used in conjunction with specialized surgical instrumentation to detect, diagnose, and repair areas of the body that were previously only able to be repaired using traditional "open" surgery.

In the past, there have been many attempts to simplify the surgeons' task of driving a needle carrying suture through body tissues to approximate, ligate and fixate them. Many prior disclosures, such as described in Drake et al, U.S. Pat. No. 919,138 issued Apr. 20, 1909, employ a hollow needle driven through the tissue with the suture material passing through the hollow center lumen. The needle is withdrawn leaving the suture material in place, and the suture is tied, completing the approximation. A limitation of these type of devices is that they are particularly adapted for use in open surgical procedures where there is room for the surgeon to manipulate the instrument.

Others have attempted to devise suturing instruments that resemble traditional forceps, such as Bassett, U.S. Pat. No. 3,946,740 issued Mar. 30, 1976. These devices pinch tissue between opposing jaws and pass a needle from one jaw through the tissue to the other jaw, where grasping means pull the needle and suture material through the tissue. A limitation of these designs is that they also are adapted primarily for open surgery, in that they require exposure of the tissues to be sutured in order that the tissue may be grasped or pinched between the jaws of the instrument. This is a severe limitation in the case of endoscopic surgery.

The term "endosurgery" means endoscopic surgery or surgery performed using an endoscope. In conjunction with a video monitor, the endoscope becomes the surgeons' new eyes from which they operate. Operations using an endoscope are significantly less invasive when compared to traditional open surgery. Patients usually return home the next day or in some cases the same day of the endosurgical procedure. This is in contrast to standard open surgical procedures where a large incision divides the muscle layers and allows the surgeon to directly visualize the operative area. Patients may stay in the hospital for 5 to 6 days or longer following open surgery. In addition, after endosurgical procedures, patients return to work within a few days versus the traditional 3 to 4 weeks at home following open surgery.

Access to the operative site using endosurgical or minimally invasive techniques is accomplished by inserting small tubes called trocars into a body cavity. These tubes have a diameter of, for example, between 3 mm and 30 mm and a length of about 150 mm (6 inches). There have been attempts to devise instruments and methods for suturing within a body cavity through these trocar tubes. Such an instrument is disclosed by Mulhollan et al, U.S. Pat. No. 4,621,640 issued Nov. 11, 1986. Mulhollan describes an instrument that may be used to hold and drive a needle, but makes no provision for retrieval of the needle from the body cavity, nor the completion of the suture by tying. Mulhollan's instrument is limited in that the arc through which the needle must be driven is perpendicular to the axis of the device. Another such instrument intended for endoscopic use is described by Yoon, U.S. Pat. No. 4,935,027, issued Jun. 19, 1990. This instrument uses oppositional hollow needles or tracks pushed through the tissue and coapted to create a tract through which the suture material is pushed. It is not clear how these curved tracks would be adapted to both be able to pierce the tissue planes illustrated, parallel to the tips of the tracks, and be curved toward each other to form the hollow tract.

The invention herein described may be used for final closure of umbilical and secondary trocar puncture wounds in abdominal tissues including the fascia and other layers. The umbilical puncture is routinely a puncture site of 10 mm to 12 mm. Future procedures may require trocar puncture sites up to 18 mm and greater in size. Due to the large size of the puncture wound, it is important that the site be closed or approximated at the interior abdominal wall following removal of the large trocar cannula. An improper or non existent closure can lead to a herniation of the bowel and/or bowel obstruction. The present mode for closure is to reach down to the desired tissue layer with a pair of needle drivers holding a needle and suture material and secure a stitch. Many patients are obese and present considerable fat in this region. Because the abdominal wall may be several inches thick, it is extremely difficult, tedious and time consuming to approximate the fascial tissues with a suture. Often times, following removal of a large trocar, the puncture site needs to be enlarged to accomplish this, thus negating some of the advantages of endoscopic surgery previously discussed.

One of the embodiments described herein may be of particular advantage in performing a surgery for correction of female stress incontinence, which affects over 5 million women in the United States. Stress incontinence is caused when the structures defining the pelvic floor are altered by aging or disturbed by the process of childbirth or other trauma. These structures in the pelvic floor normally hold the urinary bladder such that maintenance of a volume of urine in the bladder is accomplished by a combination of muscle tone and bladder positioning.

There are a number of surgical procedures that may be performed in order to restore the normal anatomical position of the urinary bladder. The classic open Burch suspension procedure is one such procedure and is a straightforward surgical treatment for correction of female stress incontinence. During this procedure, sutures are precisely placed in the wall of the vagina on each side of the urethra, with care being taken to avoid puncturing either the urethra or the mucosal layer of the vagina. These sutures are then looped through a ligament, called Cooper's ligament, which runs along the posterior ridge of the pubic bone. These sutures are then pulled taut, and carefully tied to suspend the urinary bladder in a more anatomically sound position, restoring normal urinary function and continence.

One of the problems with the procedure described above is that it is normally done only in conjunction with other scheduled abdominal surgical procedures such as a hysterectomy. This is because, as described earlier, an open surgical approach requiring a large abdominal incision must be used, and it is not very common for a patient to elect to have a major abdominal surgical procedure just for the treatment of incontinence.

Consequently, of late, a procedure known as a laparoscopic Burch suspension procedure has begun to find favor among physicians. The laparoscopic approach to the Burch procedure has all of the advantages described earlier with respect to post operative pain, hospital stay and recovery time. There are three difficulties associated with the laparoscopic approach; access, suture placement, and knot tying. The present invention addresses the problems surrounding the placement of the sutures in the appropriate structures and in the optimal position, and also addresses particular aspects of needle retrieval and knot tying when using endoscopic techniques.

Currently, the placement of sutures while using endoscopic techniques involves placing a semi-circular needle, attached to and carrying a suture, in a pair of endoscopic needle holders. These needle holders, which resemble a pair of pliers with an elongated shaft between the handles and the jaws, must be placed down through one of the surgical trocars into the body cavity containing the structure to be sutured. Because of their size, the needles used in these procedures are generally not able to be held in the jaws of the needle driver while being introduced through the operative trocar. The surgeon must hold the suture string in the needle holder jaws, and push the needle holder trailing the needle and suture into the body cavity. The suture and needle combination is dropped in the body cavity, and the needle is then located and picked up and properly positioned in the needle holder jaws. This is a difficult and time consuming aspect of the current endoscopic technique for suturing. The needle carrying the suture may then be driven by pronation of the wrist, causing rotation of the elongate shaft, and subsequent arcuate rotation of the semi-circular needle.

It may be seen that a limitation of this type of needle driver is that the needle may only be driven or rotated in a plane perpendicular to the axis of rotation, such axis being described by the elongate shaft and the position of the surgical trocar. Thus the current endoscopic needle drivers will not allow the surgeon to swing the needle in an arc parallel to the trocar's axis. This is a severe limitation in the case of the laparoscopic Burch, because of the orientation of the anatomy relative to the planes of access. The vaginal wall and the Cooper's ligament require the sutures to be placed in a orientation that makes the procedure extremely difficult and time consuming with the use of currently available instrumentation. It is also a limitation when attempting to ligate vessels, ligaments and other structures that run perpendicular to the axis of the operative trocar.

Another limitation of the current instrumentation is seen in the aspect that requires the surgeon to prepare the needle for penetration of the tissue while the needle is inside the body. This process is a time consuming, and sometimes frustrating exercise in hand to eye coordination, which is complicated by the fact that the surgeon is viewing the three dimensional space inside the body cavity through a two dimensional video monitor.

It may also be seen that the surgeon must be able to retrieve the needle trailing the suture material back through the same surgical trocar through which the needle driver is placed. This allows a knot to be tied in the suture outside of the body, and pushed down the trocar to the structure being sutured. Thus the needle driver must be able to retrieve the needle and bring the needle trailing the suture back up through the same trocar through which it is introduced allowing the tied knot to be pushed back down into the operative site.

It may also be seen that if the surgeon desires to place more than one suture throw through the tissue, he must be able to reload the needle into the needle driver. This may be done extracorporeally, that is, outside the body, in a manner similar to the initial loading of the suture device, or it may be done intracorporeally, that is, inside the body. Features which facilitate the intracorporeal loading of the needle can be seen to provide the surgeon with another option in the application of suture material to tissues, and could save operative time.

As it will be obvious to those skilled in the art, that the use of the techniques described above for the performance of the Burch bladder suspension procedure may be used for other endoscopic suturing tasks, such as for ligating vessels and ligaments during the performance of, for example, a hysterectomy or oophorectomy, or for the approximation of tissue flaps such as in the performance of procedures, for example, for the treatment of gastro-esophageal reflux disorder.

Currently, a number of manufacturers of suture materials and needles exist. There are USP (United States Pharmacopeia) standards for the suture material diameters and tensile strengths, however no similar standards exist for the suture needles. There are however, conventional "standard" needle sizes that many manufacturers fabricate. The needles are generally specified by the needle wire diameter, needle length and the bend arc length. A common needle size for most suture manufacturers, for example, is 26 mm long by ½ arc (180°). As it may be seen by geometric construction, a 26 mm×180° needle describes a fixed bend radius, and this nominal bend radius is fairly consistent from manufacturer to manufacturer. Typically, the suture material is crimped in either a U shaped channel formed in the distal portion of the needle, or in a drilled hole. The crimp zone size and configuration varies between manufacturers, and generally tends to straighten out the bend radius in that localized area. Between the manufacturing tolerances in the bend radius and the straightening of the end of the needle in the crimp zone, the repeatability of the shape of the needle and suture combination may vary significantly. It is therefore desirable to construct an needle guide channel which will both guide the needle precisely, and allow for the aforementioned manufacturing tolerances and perturbations. This would allow readily available commercial suture and needle combinations to be used with the suture placement system.

None of the prior art devices are adaptable to effect the placement of a suture in the anterior abdominal wall, nor are they adaptable to place sutures precisely and controllably while making provision for needle retrieval when using endoscopic techniques. It is therefore an object of the present invention to provide a family of novel suturing devices that overcomes the above set out disadvantages of prior known devices in a simple and economical manner.

It is a further object of the present invention to provide a suture device that will permit the approximation of the separated edges of a puncture wound without making a larger incision to expose the wound margins.

A further object of the present invention is to provide a suture device that will permit the surgeon to apply substantial force to the needle, permitting it to be driven through tough tissues, for example, a ligament or the abdominal fascia.

It is a further object of the present invention to provide a suture device that can be used in conjunction with modern day endoscopic surgical techniques.

Another object of the invention is to provide a suture device that will allow a needle to be driven in an arc which describes a plane parallel to the axis of the device.

Yet another object of the invention is to provide a suture device that may be used to approximate the edges of an internal wound. Another object of the present invention is to provide a suture device that permits the penetration of two needles having suture material extending there between into and through the sides of a wound and into catches thereby creating a suture loop through the wound that may be tied to approximate the tissues.

Another object of the invention is to provide a suture device that will permit the surgeon to place sutures around vessels, ligaments, and other structures to effect ligation.

A still further object is to provide a suture device which will provide optimal needle guidance while accommodating manufacturing tolerances and differences in needle construction and crimping.

Yet another object is to provide an articulating head to allow the needle exit angle to be adjusted to the tissues, and further, to allow sutures to be placed in heretofore inaccessible areas of the body.

It is still a further object to provide a suture device with features which allow the needle to be loaded into the suture device intracorporeally, that is, inside the body.

SUMMARY OF THE INVENTION

The present invention is a new medical device that will allow the surgeon to quickly and easily place a suture in the interior wall of a body cavity to approximate the tissues separated as a result of a puncture wound made by the introduction of a surgical trocar into a body cavity during endoscopic surgery. The invention described herein may also be used to approximate the margins of an open wound in an internal organ, such as the uterus or the stomach, such as would be effected during the course of a resection for benign or malignant lesions.

The present invention includes needle holders that releasably hold a pair of needles that are in turn attached to each end of a single piece of suture material. Such needle holders are held within tubular guiding tracks housed within a hollow outer sleeve that may be introduced into a puncture wound. The needle holders and guiding tracks may be deployed outside the hollow sleeve to allow the needles to engage the tissue to be approximated. A plunger is coupled to rigid driving members that are in turn attached to flexible driving members adapted to follow the shape of the guiding tracks. The flexible driving members are suitably attached to the needle holders. The plunger is pushed, simultaneously driving the needle pair into opposite sides of the puncture wound and into catches also disposed within the hollow sleeve. The needle holders are retracted into the guiding tracks, and the tracks pulled back into the hollow sleeve trailing the suture material. The device may then be withdrawn, leaving a loop of suture material precisely placed in the selected tissue, for example, in the interior wall of the body cavity. The needles are removed from the ends of the suture, and the suture material is tied to complete the approximation of the tissue.

In one aspect, the present invention differs from the prior art in that it allows a suture to be placed in a retrograde fashion in the puncture wounds created during the introduction of trocars used for endoscopic surgery. These puncture wounds have margins perpendicular to the plane of tissue dissection, unlike the wounds that are addressed by prior art in which the tissues generally overlap. Presently, all the existing instruments are designed to either approximate tissues to which direct visual and physical access may be gained during open surgery, or to approximate tissues that may be pinched between the jaws of a forceps like instrument. Wounds in body organs such as the uterus or the stomach which are created during the resection or removal of benign or malignant lesions may also have wound margins which require end to end approximation instead of overlapping. The present invention allows the surgeon to independently pass a needle through each side of the wound to allow the two sides to be drawn together, approximating the tissue.

The needle driver apparatus of the present invention may be constructed in a number of different ways. Several of the preferred ways are described herein. One embodiment uses needle guides which are semicircular in shape, holding either a semicircular needle, or a semicircular needle holder with a small needle tip. These guides are disposed across their diameter within a hollow tubular sleeve when in the retracted mode, and are rotated about one end to deploy them outside the bounds of the hollow sleeve for engaging the tissue to be sutured. The needles, or the needle holders, are driven through the tissue by axial movement of a rigid cylindrical member which contacts a flexible cylindrical member that follows the semicircular shape of the guide tracks. The needles are caught in catches placed within the hollow tubular sleeve that capture the needle by means of a leaf spring disposed to flex, preferably in one direction, and squeezing into grooves or recesses in the needles, thereby retaining the needles to the hollow tubular sleeve. The needle guides may be retracted, and the instrument removed from the wound, thus trailing the suture material. The needles are removed, the suture is tied, and the approximation is completed.

Another version of the device uses similar semicircular needle holders to the previous version, but the needle guides are eliminated. The needle holders are instead rotated about their axes such that the needles attached to the ends of the holders describe an arc that encompasses the tissue to be sutured.

It is contemplated that the above embodiments may be modified to include needle paths other than circular, such as helical, elliptical or straight, by modification of the needles, the needle holders and the needle guides. It is also possible to adapt the above configurations to allow each of the needles to be actuated and driven independently by dividing the deployment controls and the needle drivers into separate left and right hand members. Further, it is possible to utilize a tool that would use only a single needle and guide it through both sides of the wound as opposed to the double needle configuration described above.

Accordingly, another embodiment of the device uses a single needle which eliminates the deployment aspect of the needle guides. The needle guide track is incorporated directly into the cannular body which is particularly adapted for use in endoscopic procedures. The cannular body is of a diameter such that it may be placed through, for example, a standard 10 mm–12 mm trocar. The needle may be a long shouldered needle such as described previously, or may be a standard ½ circle, or 180° needle, with a length of, for example, 22 to 28 mm and crimped onto a length of standard suture material. As previously discussed, those skilled in the art will understand that various needle wire diameters, needle bend radii, needle cross sections, and suture materials are all adaptable to be used in the devices described herein. The needle may be loaded into the preformed needle guide track in the cannular body. It should be noted that the needle is placed in the cannular body across its diameter such that the point of the needle lies substantially perpendicular to the axis of the cannular body. As in previous embodiments, axial movement of a flexible drive member drives the needle out of the guiding track into and through tissue placed adjacent to the exit opening in the cannular member.

After having driven the needle into tissue, if the needle is a shouldered needle, it may be retrieved by using a keyhole shaped slot incorporated into the side of the cannular body. If the needle is a standard, non-shouldered needle, standard laparoscopic graspers, which have been introduced into the operative site via a secondary trocar, may be used to pull the needle up a short distance trailing the suture. The needle driver may then be used to retrieve the needle and suture combination by either pinching the suture material in a groove fashioned for that objective, or clamping the needle with a means adapted for that purpose. The needle trailing the suture may then be withdrawn through the surgical trocar.

This basic method of driving and retrieving the needle may be used in a number of ways at the surgeon's discretion to effect approximation, ligation, or fixation of tissue. Approximation involves the placement of one to multiple sutures in order to pull the edges of a wound together to effect healing. Ligation involves placing a suture circumferentially about a vessel or duct in order to tie it off. In the case of ligation, only a single suture is placed, and a knot tied to strangulate the encompassed structure. Fixation involves the placement of sutures to positionally secure tissues in a particular orientation, and may require that multiple sutures be placed. Fixation may also require that each end of the suture be driven through the tissue more than once.

As it may be apparent, provisions for needle retrieval, the capability of the needle to be reloaded into the needle guide track, and the positioning and orientation of the needle are important to being able to efficiently and effectively place sutures for various therapeutic reasons. The invention herein described solves these problems.

The above described embodiments may be modified to include a needle carrier adapted as described before to hold a short barbed needle. This carrier may be disposed within the preformed needle guide track in the cannular body. A similar catch mechanism as described previously is incorporated into the side of the cannular body at the end of the arcuate path described by the short needle/needle carrier combination when axial movement of the flexible drive member drives the needle and carrier combination out of the guide and through the tissue to be sutured. Use of this embodiment for closure of trocar puncture wounds can be accomplished by loading one end of a suture prepared with short needles at both ends into the needle carrier. The instrument is inserted into the puncture wound by means of the trocar placed therein. The instrument is located such that the tip of the needle is placed directly against the inside of the abdominal wall.

The needle is driven up into the abdominal fascia by the flexible needle driver coupled to the needle driver button, and into the catch. The short needle stays in the catch, the needle carrier is withdrawn back into the needle guide track, and the entire device is withdrawn from the surgical trocar. The needle is removed from the catch, the opposite end of the suture with its attached short needle is loaded into the instrument, and the entire process is repeated with the second end of the suture being driven into the tissue on the opposite side of the puncture wound, 180° from the initial stitch. The instrument and trocar are removed from the wound, and the remaining loop of suture is tied to approximate the tissues, thus closing the wound.

As it may be appreciated, this embodiment may be used in order to effect suturing in many different parts of the body, and is not limited to the closure of the wounds caused by the insertion of operative trocars into a body cavity. With the availability of both absorbable and non-absorbable suture material attached to the short needles, it is contemplated that the above described embodiment may be used in performance of procedures such as, for example, the laparoscopic Burch previously described. It is also contemplated that ligation of vessels and ligaments, such as, for instance, the ligation of uterine vessels and ligaments during the performance of a hysterectomy may be accomplished with this embodiment. This embodiment may also find application in the repair of the meniscal tissue in the knee or shoulder. It is to be clearly understood that this embodiment eliminates the manual step of needle retrieval from the wound, as the needle is automatically captured by the instrument itself.

It may also be appreciated that the limitations of the angles of access and the restrictions on the lateral manipulation of instruments used during endoscopic procedures imposed by the operative trocars can make reaching certain anatomical structures difficult. Thus, the ability to articulate an instrument within the body cavity independent of the manipulation of the main body shaft can be of particular advantage in accessing these difficult to reach structures. By articulating the head of the needle driver instrument, the exit angle of the needle may be adjusted, as well as opening the possibility of accessing certain areas of the body which are inaccessible in a linear fashion due to the aforementioned mechanical constraints.

In one embodiment, the present invention is a suturing instrument comprising: an elongate body member having a longitudinal axis; a deployment controller having a proximal end and a distal end, the deployment controller extending substantially along the longitudinal axis of the elongate body member to a distal end of the elongate body member, wherein the deployment controller has a retracted position and a deployed position; and a needle deployment system located within the distal end of the elongate body member and coupled to the deployment controller, the needle deployment system comprising: a curved surgical needle slidably positioned in a curved needle channel within the elongate body member, the curved needle channel located substantially in a plane which is substantially parallel to the elongate body member longitudinal axis, the curved needle channel having a needle retention zone with a needle retention zone cross sectional dimension and a needle guidance zone with a needle guidance zone cross sectional dimension, the needle guidance zone cross sectional dimension smaller than the needle retention zone cross sectional dimension; and a flexible pusher coupled to the distal end of the deployment controller, the needle deployment system having a retracted configuration when the deployment controller is in the retracted position wherein substantially all of the curved surgical needle is contained within the elongate body member and a deployed configuration when the deployment controller is in the deployed position, wherein the flexible pusher pushes the curved surgical needle through the curved needle channel outside of the elongate body member along a path having an initial direction away from the elongate body member longitudinal axis as the deployment controller begins to move from the retracted position toward the deployed position followed by a direction toward the elongate body member longitudinal axis as the deployment controller approaches the deployed position.

In another embodiment, the present invention is a suturing instrument comprising: an elongate body member having an internal driver pathway extending along an elongate body member longitudinal axis from a proximate end to a distal end of the elongate body member, the internal driver pathway comprising a substantially linear pathway section which is substantially parallel with the longitudinal axis connected to a substantially C-shaped pathway section near the distal end of the elongate body member; a substantially C-shaped needle channel located at the distal end of the elongate body member and connected to the C-shaped pathway section of the internal driver pathway such that the combination of the C-shaped pathway section of the internal driver pathway and the C-shaped needle channel form a substantially S-shaped pathway having a laterally disposed exit from the elongate body member distal end; and a needle driver member slidably disposed within the internal driver pathway. This device may further include a flexible driver member coupled to the needle driver member, the flexible member slidably disposed in the C-shaped pathway section of the internal driver pathway. In some embodiments, the C-shaped needle channel is substantially semi circular. In other embodiments, the C-shaped curved needle channel further comprises a needle retention zone with a needle retention zone cross sectional dimension and a needle guidance zone with a needle guidance zone cross sectional dimension, the needle guidance zone cross sectional dimension being smaller than the needle retention zone cross sectional dimension.

In yet another embodiment, the invention is a suturing instrument comprising: an elongate body member, the elongate body member having a substantially straight distal end portion; and a concave curved driver pathway coupled to a convex curved needle channel located within the substantially straight distal end portion of the elongate body member. In some embodiments, the concave curved driver pathway is substantially C-shaped and the convex curved needle channel is substantially C-shaped and the C-shaped concave curved driver pathway is connected to the C-shaped convex curved needle channel such that the combination of the C-shaped concave curved driver pathway and the C-shaped convex curved needle channel form a substantially S-shaped pathway having a laterally disposed exit from the elongate body member distal end portion. Some embodiments further include a flexible driver member slidably disposed in the concave curved driver pathway. In other embodiments, the convex curved needle channel is substantially semi circular. In some embodiments, the convex curved needle channel further comprises a needle retention zone with a needle retention zone cross sectional dimension and a needle guidance zone with a needle guidance zone cross sectional dimension, the needle guidance zone cross sectional dimension being smaller than the needle retention zone cross sectional dimension.

In another aspect, the invention is a passive needle catch for receiving and retaining a shouldered surgical needle, the catch comprising a substantially planar foundation in which is formed at least one flexible aperture, wherein a lateral dimension of the flexible aperture is larger on a first side of the foundation than on a second side of the foundation, wherein the flexible aperture expands to allow passage of the needle shoulder into the aperture and contracts after the needle shoulder has passed through the aperture.

In yet another aspect, the invention includes a needle catch made by the process comprising the steps of: selecting an aperture pattern; and etching the aperture pattern in a planar substrate. In some embodiments, the etching step further comprises the step of etching the substrate from a single side.

The invention further includes a suturing instrument comprising: an elongate body member having a longitudinal axis; a deployment controller having a proximal end, a distal end, a retracted position and a deployed position, the deployment controller extending substantially along the longitudinal axis of the elongate body member to a distal end of the elongate body member; and a needle deployment system located within the distal end of the elongate body member and coupled to the deployment controller, the needle deployment system comprising: a curved needle carrier channel; a curved needle carrier movably positioned in the curved needle carrier channel, the curved needle carrier having a mount for a needle point on a distal end and a peripheral groove along a portion of its periphery extending from a proximate end of the curved needle carrier; and a flexible pusher coupled to the deployment controller at one end and to the curved needle carrier at another end such that the flexible pusher engages the curved needle carrier peripheral groove as the deployment controller moves from the retracted position to the deployed position whereby the flexible pusher pushes the curved needle carrier through the curved needle channel.

In yet another embodiment, the invention is a suturing instrument comprising: an elongate body member having a longitudinal axis; a curved needle channel located within the elongate body member at a distal end thereof, the curved needle channel located substantially in a plane which is substantially parallel to the elongate body member longitudinal axis, the curved needle channel forming a needle exit port in a side wall of the body member; and a suture slot formed in the body member distal end wherein the suture slot intersects the needle exit port and the curved needle channel periphery along a substantial portion of the length of the curved needle channel, wherein the suture slot has a width which is selected to be substantially smaller than a lateral dimension of the needle channel such that a length of suture can be inserted into the curved needle channel through the slot and the needle exit port.

An additional embodiment is a suturing instrument comprising a curved needle channel having a needle retention zone with a needle retention zone cross sectional dimension and a needle guidance zone with a needle guidance zone cross sectional dimension, the needle guidance zone cross sectional dimension being smaller than the needle retention zone cross sectional dimension.

Yet another embodiment of the invention is a suturing instrument comprising: an elongate body member having a longitudinal axis; a deployment controller having a proximal end and a distal end, the deployment controller extending substantially along the longitudinal axis of the elongate body member to a distal end of the elongate body member, wherein the deployment controller has a retracted position and a deployed position; and a needle deployment system located within the distal end of the elongate body member and coupled to the deployment controller, the needle deployment system comprising: a curved surgical needle slidably positioned in a curved needle channel within the elongate body member, the curved needle channel located substantially in a plane which is substantially parallel to the elongate body member longitudinal axis; and a flexible pusher coupled to the distal end of the deployment controller, the needle deployment system having a retracted configuration when the deployment controller is in the retracted position wherein substantially all of the curved surgical needle is contained within the elongate body member and a deployed configuration when the deployment controller is in the deployed position, wherein the flexible pusher pushes the curved surgical needle through the curved needle channel outside of the elongate body member along a path having an initial direction away from the elongate body member longitudinal axis as the deployment controller begins to move from the retracted position toward the deployed position followed by a direction toward the elongate body member longitudinal axis as the deployment controller approaches the deployed position. This embodiment may further comprise: a suture channel which intersects the curved needle channel at the distal end of the elongate body member; and a suture capture projection positioned adjacent the suture channel and the curved needle channel such that a suture lying in the suture channel is captured between the projection and the flexible pusher as the deployment controller moves from the retracted position to the deployed position.

Another embodiment of the present invention is a suturing instrument comprising: an elongate body member having a longitudinal axis; a deployment controller having a proximal end and a distal end, the deployment controller extending substantially along the longitudinal axis of the elongate body member to a distal end of the elongate body member, wherein the deployment controller has a retracted position and a deployed position; and a needle deployment system located within the distal end of the elongate body member and coupled to the deployment controller, the needle deployment system comprising: a curved needle carrier channel and a curved needle carrier movably positioned therein and having a needle point mounted on a distal end thereof, the curved needle channel located substantially in a plane which is substantially parallel to the elongate body member longitudinal axis; and a flexible pusher coupled to the deployment controller, the needle deployment system having a retracted configuration when the deployment controller is in the retracted position wherein substantially all of the curved needle carrier is contained within the elongate body member and a deployed configuration when the deployment controller is in the deployed position, wherein the flexible pusher pushes the curved needle carrier along the curved needle channel outside of the elongate body member along a path having an initial direction away from the elongate body member longitudinal axis as the deployment controller begins to move from the retracted position toward the deployed position followed by a direction toward the elongate body member longitudinal axis as the deployment controller approaches the deployed position. Furthermore, this embodiment may include a bullet needle having a suture attachment point, the bullet needle inserted in the curved needle carrier; a suture attached to the bullet needle suture attachment point; and a needle capture system located on the elongate body member at a location which intercepts the portion of the needle carrier path which approaches toward the elongate body member.

Yet another embodiment is for a suturing instrument for placing sutures inside a body cavity comprising: an elongate body member having a longitudinal axis; needle deployment means for deploying a surgical needle outside a distal end of the elongate body member along a path having an initial direction away from the elongate body member longitudinal axis followed by a direction toward the elongate body member longitudinal axis; and needle capture means attached to the elongate body member for capturing the surgical needle after deployment. This embodiment may further include a knot pushing means located at the distal end of the elongate body member for pushing a knot tied extracorporeally into the body cavity.

These and other characteristics of the present invention will become apparent through reference to the following detailed description of the preferred embodiments and accompanying drawings.

BRIEF DESCRIPTION OF THE DRAWINGS

These and other objects and advantages of the subject invention will become more fully apparent from a reading of the following description in conjunction with the drawings wherein:

FIGS. 1A through 1H illustrate the general structure and operation of a first embodiment of the present invention.

FIG. 2 is a detail perspective view of a needle showing ridges on the needle to secure the needle in the catch.

FIGS. 4A and 4B are plan views of the suturing device described in FIG. 3 illustrating the operation thereof.

FIGS. 5A and 5B are detail plan views of the distal end of the suturing device described in FIGS. 4A and 4B illustrating the use of a shouldered needle.

FIG. 5C is a detail plan view of the distal end of the suturing device described in FIGS. 4A and 4B illustrating the use of a standard non-shouldered needle.

FIGS. 5D and 5E are detail plan views of the distal end of the suturing device described in FIGS. 4A and 4B illustrating a modification to the needle guide track to accommodate the use of a standard non-shouldered needle with a straight crimp section.

FIG. 6 is a detail perspective view of an alternate catch mechanism with a needle.

FIG. 7 is a detail perspective view of a suture catch mechanism with a length of suture.

FIG. 8 is a detailed perspective view of the end of the suturing device illustrating its use for pushing knots tied in suture.

FIG. 8A is a detailed plan view of an alternate embodiment of a suture device illustrating features for use for pushing knots tied in suture.

FIGS. 9A and 9B are detailed cross sectional views illustrating the general structure and operation of an alternate embodiment of a needle delivery and capture system.

FIGS. 9C and 9D are detailed cross sectional views illustrating the general structure and operation of another alternate embodiment of a needle delivery and capture system.

FIG. 10 is a projected detail view taken along the lines of view 10—10 of FIG. 9A illustrating the needle catch.

FIG. 11 is a cross sectional view taken along the lines of 11—11 on FIG. 10.

DETAILED DESCRIPTION OF THE PREFERRED EMBODIMENTS

Although the principles of the present invention are applicable to any device suitable for use in surgical procedures, whether performed on humans or animals, particular utility is effected in human abdominal surgery performed using endoscopic techniques for closure of the wounds created during the introduction of trocars into the abdominal cavity, and particularly the puncture wounds created thereof, as well as closure or approximation of the wounds created either during the resection of benign or malignant lesions, or during the performance of other therapeutic procedures on an organ or organs within a body cavity.

Figure 1C:
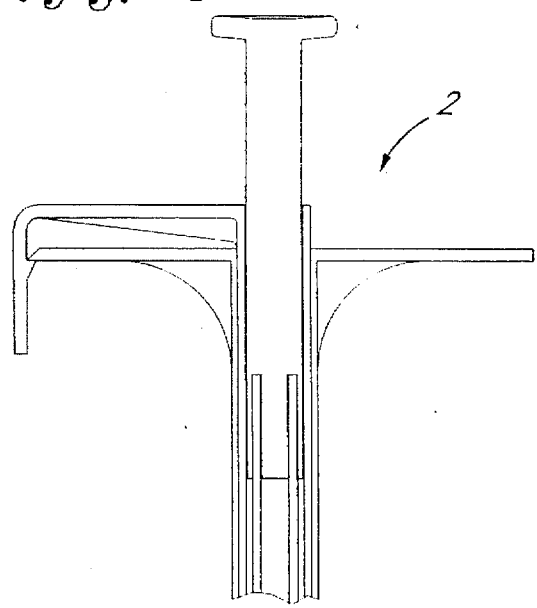
Figure 1D:
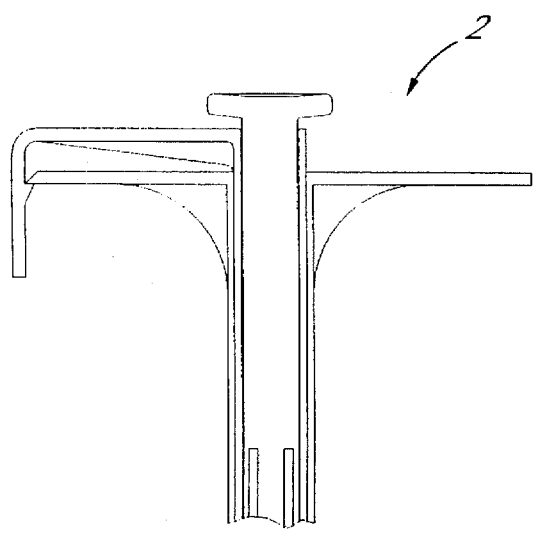
Figure 1E:
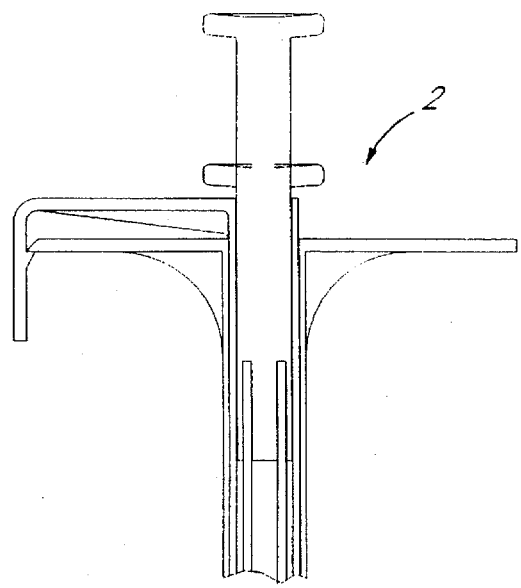
Figure 1F:
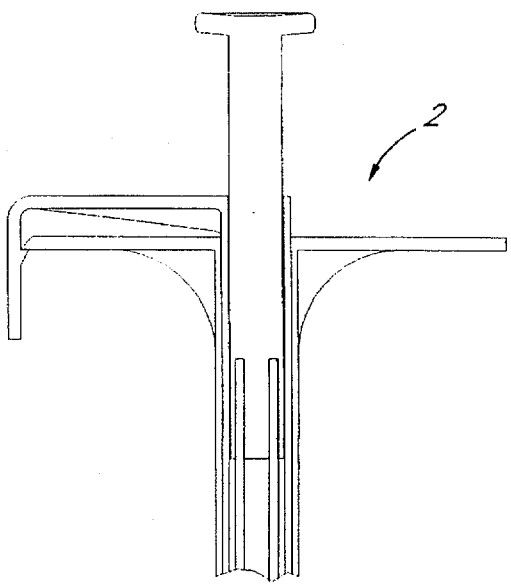

FIGS. 1A through 1H illustrate the general structure and operation of the present invention. FIGS. 1A and 1B show a device 2, according to the present invention, which incorporates a length of standard suture material 4 with a needle 6 on each end. The needles 6 are held by a needle carrier 8 (FIG. 1D) and loaded into two guiding tracks 10. The guiding tracks 10, containing the needle carriers 8 and needles 6, are deployable outside a housing 12 of the device 2 to allow the suture material 4 to be placed outside the limits of a puncture wound 14 (FIGS. 1B and 1C). After deployment of the guiding tracks 10 (with the needle carriers 8 and needles 6 contained within) the needle carriers 8 and needles 6 are driven out of the guiding tracks 10 and into tissue surrounding the puncture wound 14 (FIGS. 1C and 1D). The needles 6 are driven into a catch mechanism 16 (FIG. 1D). The needle carriers 8 are retracted back into the guiding tracks 10 (FIG. 1E). The guiding tracks 10 (now containing only the needle carriers 8 without the needles 6 and the catch mechanism 16 with the captured needles 6, are retracted as shown in FIGS. 1F, 1G and 1H. With a loop of suture 4 having thus been placed in the tissue surrounding the puncture wound 14, the suture device 2 is removed from the wound 14, thereby pulling the ends of the suture 4 with it (FIG. 1H). Closure of the puncture wound 14 is accomplished by cutting the suture 4 to remove the needles 6, tying a knot in the suture 4, and pushing it into the wound 14. Superficial closure is then performed by normal means according to the surgeon's preference.

FIG. 2 shows a detail view of a needle 166 secured to a suture 168 as it enters a catch 174 through a slot 186 created by spring leaves 188a and 188b. The catch 174 is preferably made of thin gauge spring steel to allow the leaves to be flexible yet create a gripping force on the needle. Ridges 190 on needle 166 enable the catch 174 to capture and hold the needle 166. The capture and holding of the needle 166 by the catch 174 is facilitated by the spring leaves 188 being disposed to bend away from the axis of needle penetration, thus snapping into the ridges 190.

Figure 2A:
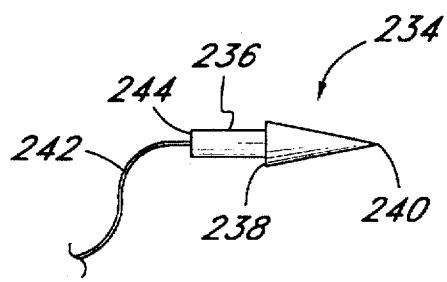
FIG. 2A is a detail plan view of an alternate needle.
Figure 2C:
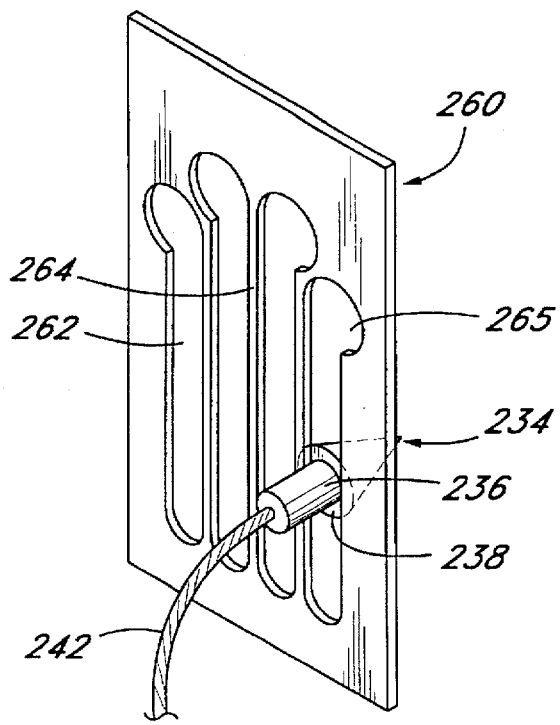
FIG. 2C is a detail perspective view of an alternate catch mechanism with a needle.
Figure 2B:
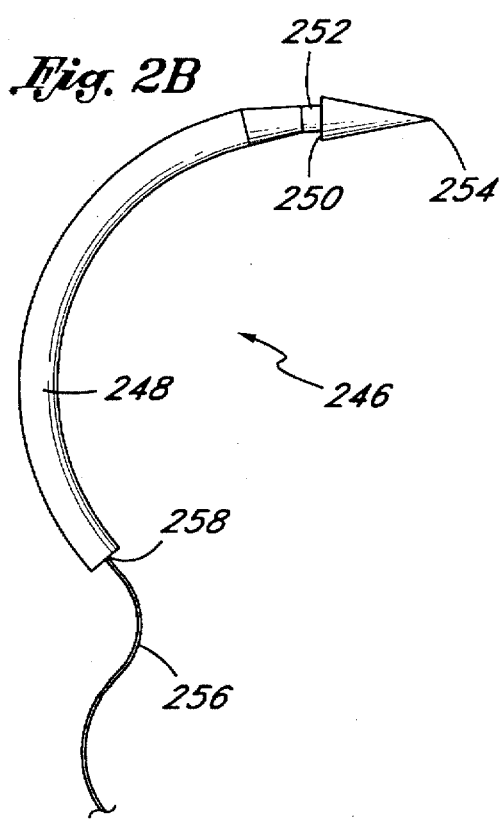
FIG. 2B is a detail plan view of another alternate needle.

FIGS. 2A through 2B show detail plan views of alternate needle embodiments. Referring to FIG. 2A, a needle 234 comprises a body 236, and a shoulder 238 tapering to a point 240. A length of suture material 242 is inserted into a hole 244 and attached to the needle 234 thereby. Referring now to FIG. 2B, a needle 246 comprises a body 248 and a shoulder 250 formed by a groove 252 which tapers to a point 254. A length of suture material 256 is inserted into a hole 258 and attached to the needle 246 thereby.

Figure 2D:
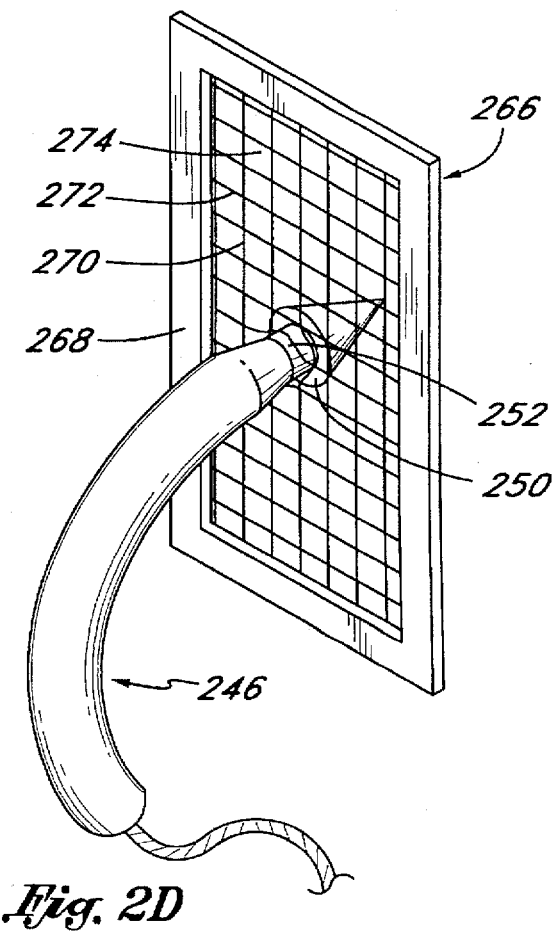
FIG. 2D is a detail perspective view of another catch mechanism with a needle.

FIGS. 2C through 2D show detail perspective views of alternate catch embodiments and illustrate their operation. A catch 260 is preferably constructed of thin stainless steel of high temper, such as ANSI 301 full hard. Although the catch 260 may be fabricated by means of stamping or laser machining, the preferred method is by chemical etching. Referring to FIG. 2C, the catch 260 includes openings 262 defined by ribs 264. As the needle 234 enters the opening 262, the ribs 264 deflect slightly to allow the shoulder 238 to pass through. After the shoulder 238 has passed the ribs 264, the ribs spring back to their original position defining the openings 262. The openings 262 are chosen to be smaller in dimension than the shoulder 238. This causes the catch 260 to retain the needle 234 by the interference between the shoulder 238 and the ribs 264 around the body 236. When it is necessary to remove the needle 234 from the catch 260, it may be moved toward an opening 265 which is sized to allow the needle shoulder 238 to pass through without resistance.

Referring now to FIG. 2D, a catch includes a frame 268 to which is attached a woven mesh 270. Threads 272 creating the woven mesh 270 may be made out of nylon or polyester or the like woven in a common over/under pattern. The weaving of the threads 272 creates holes 274 in the mesh through which a needle 246 may be passed. The needle 246 is constructed such that the shoulder 250 defined by the groove 252 is larger than the holes 274, or conversely, the holes 274 are chosen to be smaller than the shoulder 250. The point 254 of the needle 246 pushes the threads 272 aside creating room for the shoulder 250 to pass through the holes 274. As the threads 272 return to their original positions, the catch 266 holds onto the needle 246 by means of the mismatch in the size of the holes 274 and the shoulder 250.

It may be seen and should be understood that catches 260 and 266 are capable of catching either needle 234 or 246. The examples of needle 234 coupled with catch 260 and needle 246 coupled with catch 246 are given purely to illustrate the concepts of each embodiment and do not exclude their coupling with alternate designs.

Figure 3:
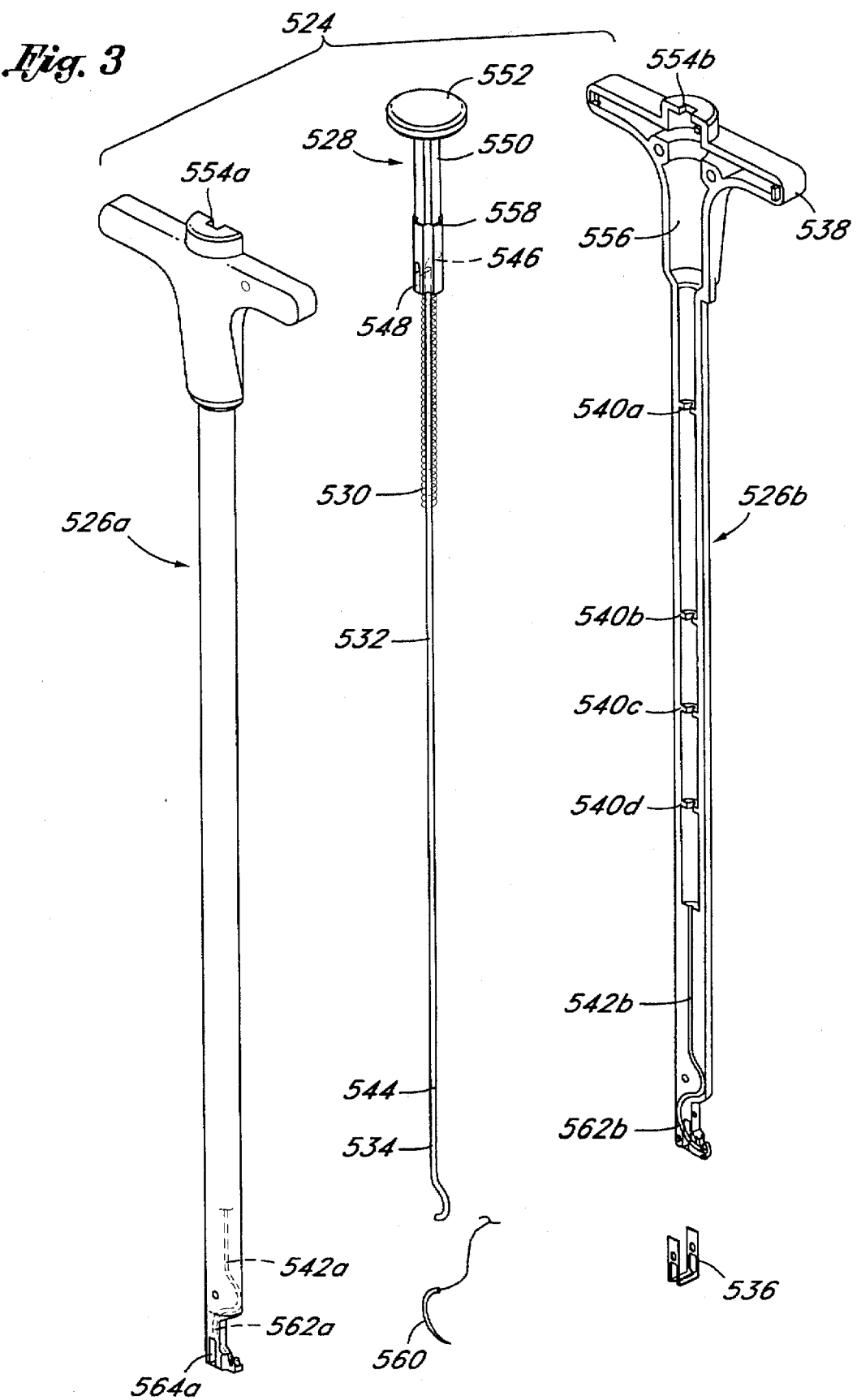
FIG. 3 is an exploded perspective view of a second embodiment of a suturing device.

Another embodiment of a suture device is described by referring to FIG. 3. A needle driver 524 is comprised of body halves 526a,b, a needle driver button 528, a compression spring 530, a rigid tube 532, a flexible needle driver 534 and a needle catch 536. The housing half 526b includes a handle 538 and guide ribs 540a,b,c,d for the rigid tube 532. The guide rib 540a also serves as a spring perch for the compression spring 530. A continuous pathway 542a,b is formed in each of the body halves 526, and when mated together they form a cylindrical cross section. The flexible needle driver 534, which may be made from a suitable flexible thermoplastic material such as nylon, polyester or polypropylene, may be crimped or attached by other mechanical or adhesive means to the rigid tube 532 at end 544. The rigid tube 532 is bent at the other end to form a hook 546, which sits in a pocket 548 in the needle driver button 528, capturing the rigid tube 532. The needle driver button 528 includes a shaft 550 which has a cruciform shaped cross section to prevent rotation of the needle driver button 528 when it is slidably engaged in the annulus formed by anti rotation boss 554a,b and a needle driver button pocket 556. The needle driver button 528 also includes a button head 552 and a shoulder 558. The shoulder 558 is dimensioned to provide a backstop such that when the needle driver button 528 is assembled into the needle driver button pocket 556, and the compression spring 530 is loaded against the guide rib 540a, the needle driver button 528 is restrained from being pushed out of the needle driver button pocket 556 by interference between the shoulder 558 and the anti rotation boss 554. The rigid tube 532 and the flexible needle driver 534 are slidably disposed within the continuous pathway 542. A needle 560 is dimensioned to slidably and rotationally fit a needle groove 562a,b which is part of the continuous pathway 542. When body halves 526 are assembled, the needle catch 536 clips into catch groove 564a,b, and may be retained by heat staking, ultrasonic welding, adhesive bonding or the like. The needle catch 536 provides the end of the needle driver 524 with a means of keeping the body halves 526 from separating.

Use of the needle driver 524 shown in FIG. 3 will now be described by referring to FIGS. 4A and 4B, and FIGS. 5A, 5B, and 5C. There may be seen a needle driver 524 comprising a cannular body 566 with finger grips 568a,b. FIGS. 4A and 5A depict the needle driver 524 as it would appear ready for use with the needle 422 loaded into the needle groove 562. A suture 570 is attached to the needle 422 as previously described. The flexible needle driver 534 rests slidably disposed within the continuous pathway 542. An end 572 of the flexible needle driver 534 rests against a crimp 574 on the attachment end of the needle 422 and the suture 570. Referring now to FIGS. 4B and 5B, it may be seen that as the needle driver button 528 is depressed by pushing on the button head 552, the rigid tube 532 is caused to move axial to the cannular body 566, sliding within the continuous pathway 542, and causing the flexible needle driver 534 to move commensurately. The needle 422 is forced to move out of the needle groove 562 trailing the suture 570 as the flexible needle driver 534 follows the continuous pathway 542. FIG. 5C illustrates a needle 560, without a shoulder such as that described for the needle 422, and a suture 576 being driven in a manner similar to that described in FIGS. 5A and 5B.

As previously described, different manufacturers of needles have different crimping equipment and styles, and coupled with the manufacturing bend tolerances, create needles that may differ considerably in their dimensional configuration. The needle groove 562 as described in the above embodiments is limited in the amount of dimensional variation that can be accommodated. In the above embodiments, the needle groove 562 is of constant circular cross section. In order to allow for the aforementioned differences in needle dimensions, the cross sectional diameter may be increased. If this is done, the precision with which the needle is guided is compromised because of the increase in clearance between the needle body and the needle groove wall. It may be seen, then, that a need exists to be able to both accommodate dimensional variations and still guide the needle with precision. We will now describe a means for doing so.

Referring to FIGS. 5D and 5E, which are detail plan views of a suture device similar to those described in FIGS. 5A–5C, there may be seen a suture application device 900 which includes a continuous pathway 902, within which resides slidably disposed a rigid tube 904 attached to a flexible needle driver 906. The continuous pathway includes a needle groove 908, which is further comprised of an exit opening 910, a needle guidance zone 912 and a needle retention zone 914. There further may be seen a curved surgical needle 916, to which is attached a suture 918 by means of a crimp in a crimp zone 920. As it may be seen in FIG. 5D, the crimp zone 920 is a straight section of the curved surgical needle. This straightness is a perturbation in the otherwise arcuate configuration of the curved surgical needle 916, and as previously mentioned, causes the axially projected cross sectional area of the curved surgical needle 916 to be increased. As may be seen in FIG. 5E, as the curved surgical needle 916 is loaded into the needle groove 908 through the exit opening 910, the increase in the cross sectional area of the needle retention zone 914 accommodates the crimp zone 920 of the curved surgical needle 916. The cross sectional area of needle guidance zone 912 is kept to a minimum in order to provide precise guidance for the curved surgical needle 916, much as a bushing with minimal clearance will guide a rod. Thus it may be seen that dimensional variations may be accommodated without severely compromising needle guidance.

It is important to the successful completion of any suturing application to be able to tie a knot in the suture after it has been placed. It is particularly important in endoscopic applications to bring the suture ends back up through the same surgical trocar through which they were introduced. This allows a knot to be tied extracorporeally, i.e. external to the body, and then pushed down through the surgical trocar to the tissue being sutured. Accordingly, we now describe various means and methods for retrieving the needle and suture combination with the same device used for driving the needle, and provisions for pushing a knot back down the surgical trocar into the wound.

FIG. 6 shows a detail perspective view of an embodiment of a catch on the end of a suture application device 580 which includes a cannular body 582 and a needle catch 584. The needle catch 584 is preferably constructed of thin hardened stainless steel of high temper, such as ANSI 301, includes slots 588a,b and openings 586a,b. The needle catch 584 is dimensioned such that the openings 586 are sufficiently large to allow the point 424 and the shoulder 426 of the needle 422 to easily pass through. After the needle 422 has been driven into tissue, the suture application device 580 may be manipulated to allow the point 424 and the shoulder 426 of the needle 422 to enter the opening 586 as illustrated in FIG. 6. The suture application device 580 may then be moved to allow the needle 422 to slide down into the slot 588 which is sized such that the shoulder 426 may not pass through. Thus the needle 422 may be captured selectively at the discretion of the user, and may be withdrawn from the surgical trocar to effect knot tying or other manipulation of the needle/suture combination.

Yet another embodiment of the present invention allowing the capture and withdrawal of the needle and suture combination is shown in FIG. 7, which shows a detailed perspective cross sectional view of the end of the suture application device 580 described in FIG. 6. Referring to FIG. 6, it may be seen that the cannular body 582 is comprised of housing halves 590a,b. In the interest of clarity, FIG. 7 shows a cutaway view of the housing halves 590, which are configured to form a needle guide track 592 and a flexible needle driver guide track 594. The needle guide track 592 and the flexible needle driver guide track 594 are continuous semi-circular grooves in the housing halves 590, and when the housing halves 590 are assembled, the flexible needle driver guide track 594 and the needle guide track 592 form a continuous pathway 596 of circular cross section in which a flexible needle driver 598 is slidably disposed and may travel to an exit opening 600. Slots 602a,b intersect with the needle guide track 592 at path bottom 604, defining projections 610a,b. The flexible needle driver 598 may optionally have a needle driver tip 606 which may be made from a different material than the flexible needle driver 598, such as stainless steel or a harder thermoplastic material. This may be helpful to improve the wear characteristics of the tip of the flexible needle driver 598. When a suture 608 is positioned in the slots 602a and 602b and rests on the path bottom 604, the flexible needle driver 598 can be advanced in the needle guide track 592 to pinch the suture 608 between the needle driver tip 606 and the projections 610a,b. The suture 608 may then be maneuvered as desired by the user, including being withdrawn through the surgical trocar. Needles of any description may be attached to the suture just described, therefore it may be seen that this mechanism and method of retrieval of a suture from the endoscopic operative field does not require a special needle with a shoulder.

As previously mentioned, in order to complete any suturing application, a knot must be tied to secure the suture material to the tissue. We now describe a simple means for facilitating the tying of knots during endoscopic procedures. Referring to FIG. 8, there is seen a suture applicator tip 690 which includes housing halves 692a,b. At the distal end of the suture applicator tip 690 are concave recesses 710a,b, which may also be seen in plan view in FIG. 8A. The suture 622 includes ends 712a,b and a knot 714, and passes through tissue 716. It is to be understood that the suture applicator tip 690 has been passed into an interior body cavity, such as the abdominal cavity, through a surgical trocar. The knot 714 in the suture 622 has been tied extracorporeally, i.e. external to the body cavity, and with the use of the suture applicator tip 690, has been guided through the surgical trocar by the concave recesses 710 to the position shown in FIG. 8. The user, by keeping tension on the ends 712a,b of the suture 622, and by pushing on the suture applicator tip 690, may guide the knot 714 further down to the tissue 716. To complete the tying of a knot, the suture applicator tip 690 is removed from the surgical trocar and another loop or knot is tied extracorporeally, and pushed down the surgical trocar in like manner to that described above. Thus it may be seen that the present invention may be used to drive the needle, retrieve the needle from the tissue, and facilitate the placement of knots to complete the approximation, ligation, or fixation.

An alternate embodiment of the knot pusher may be seen by referring to FIG. 8A. There may be seen a cannular body 756 which includes protrusions 758a,b and a land 760. The protrusions 758a,b and the land 760 combine to form a pocket 762, which may function in a similar manner to the concave recesses 710 described in FIG. 8. It should thus be clear that guidance of the suture for the purposes of knot tying may be accomplished by means of either a pocket formed by protrusions or other positive external features such as ribs or bumps on the end of the cannular body, or by recesses or other negative external features such as depressions, concavities, or reliefs formed in the end of the cannular body.

Yet another embodiment of the invention is an alternate needle driver and catch system as shown in FIG. 9A and FIG. 9B, which are detailed cross sectional views of the distal end of the suture application system. Referring to FIG. 9A a cannular body 718 is comprised of the housing halves 720a,b. It is to be understood that for clarity only one of the housing halves 720 of the cannular body 718 is shown in FIG. 9A and FIG. 9B. The housing halves 720 are configured to create a guided pathway 722 which is comprised of a needle carrier guide track 724 and a flexible carrier driver guide track 726. A needle carrier 728 and flexible carrier driver 730 are joined at an end 732 of the needle carrier 728. The attachment between the needle carrier 728 and the flexible carrier driver 730 at the end 732 can be accomplished by crimping, welding, adhesive bonding or various other techniques. A bullet needle 734 includes a shoulder 736, a point 738 and a shaft 740. A length of suture material 742 is attached to the shaft 740 by placing it in a hole 744 and holding it there by suitable means, such as crimping or adhesive bonding or the like. Further incorporated in the housing halves 720 are catch pockets 746a,b which position and retain a needle catch 748. Referring to FIG. 10, which is a detail plan view taken along the lines of 10—10 of FIG. 9A, it may be seen that the needle catch 748 includes openings 750 defined by ribs 752. The configuration and function of the needle catch 748 is similar to that described earlier in FIG. 2C. The bullet needle 734 is inserted into an end 754 of the needle carrier 728. The shoulder 736 of the bullet needle 734 rests on the end 754 of the needle carrier 728, said end 754 dimensioned to hold and retain the bullet needle 734 in a manner previously described. When the catch 748 is fabricated by means of chemical etching, the most preferred method is to etch from a single side, known in the art as single sided etching. When the catch 748 is etched from a single side, the ribs 752 have a tapered cross section 753 as shown in FIG. 11, which is a detail cross sectional view taken along the lines of 11—11 of FIG. 10. The tapered cross section 753 helps to guide the needle 734 into the catch openings 750, minimizing the chance of the needle 734 hitting the top of the ribs 752.

Referring now to FIGS. 9A and 9B, the operation of this embodiment will be described. It is to be understood that the function of this embodiment is similar to that previously described in FIGS. 1A through 1H, that is, to approximate and close the puncture wounds created when surgical trocars are introduced into a body cavity. For clarity, the imposition of tissue planes along the path of needle travel to be described in FIGS. 9A and 9B has not been shown, although it is implied. FIG. 9A shows the bullet needle 734 loaded into the needle carrier 728 which is depicted in the retracted position. In this position, the cannular body 718 may be passed through a surgical trocar and into a body cavity for operation of the device. As shown in FIG. 9B, as the flexible carrier driver 730 is advanced into the needle guide track 724, the needle carrier 728, holding the bullet needle 734 and trailing the suture 742 is driven on a semi-circular path terminating in the needle catch 748. The bullet needle 734 is captured by the catch 748 in a manner previously described in FIG. 2C. The flexible carrier driver 730 may be retracted back into the flexible carrier driver guide track 726, causing the needle carrier 728 to rotate back into the needle carrier guide track 724 in the body half 720. The instrument may be removed from the surgical trocar, and the process repeated on the other side of the wound, and after knots have been tied, an approximation of the puncture wound is accomplished. It may be seen that a knot pusher such as that described in FIG. 8 may be incorporated into the distal end of this embodiment of the suture applicator to effect the tying of knots for approximation of the puncture wounds. As such, the knots would be pushed directly into the wound, and not necessarily through the surgical trocar.

Yet another embodiment of the invention is an alternate needle driver and catch system as shown in FIG. 9C and FIG. 9D, which are detailed cross sectional views of the distal end of the suture application system and are similar in construction to those already described in FIGS. 9A and 9B. Referring to FIG. 9C, a cannular body 770 is comprised of the housing halves 772a,b. It is to be understood that for clarity only one of the housing halves 772 of the cannular body 770 is shown in FIG. 9C and FIG. 9D. The housing halves 772 are configured to create a guided pathway 774 which is comprised of a needle carrier guide track 776 and a flexible carrier driver guide track 778. A needle carrier 780 and flexible carrier driver 782 are joined at saddle 784 of the needle carrier 780. The saddle 784 comprises a channel, groove or opening formed in the proximate end of the needle carrier 780 into which the flexible carrier driver 782 may enter circumferentially as opposed to axially. The attachment between the needle carrier 780 and the flexible carrier driver 782 at the saddle 784 can be accomplished by crimping, welding, adhesive bonding or various other techniques. A bullet needle 786 includes a shoulder 788, a point 790 and a shaft 792. A length of suture material 794 is attached to the shaft 792 by placing it in a hole 796 and holding it there by suitable means, such as crimping or adhesive bonding or the like. Further incorporated in the housing halves 772 are catch pockets 798a,b which position and retain a needle catch 800. The configuration and function of the needle catch 800 is similar to that described earlier in FIG. 2C. The bullet needle 786 is inserted into an end 802 of the needle carrier 780. The shoulder 788 of the bullet needle 786 rests on the end 802 of the needle carrier 780, said end 802 dimensioned to hold and retain the bullet needle 786 in a manner previously described.

Although the operation of this embodiment is virtually identical to that described in FIGS. 9A and 9B, there are improvements included in this embodiment to the overall operation of the suture system. Referring back to FIGS. 9A and 9B, as it may be appreciated, as the needle carrier 728 approaches the end of its stroke, as illustrated in FIG. 9B, the circumferential length of the needle carrier 728 left inside the needle carrier guide track 724 is quite minimal. This can allow the needle carrier 728 holding the needle 734 to drift off of the predescribed arcuate path which terminates in the needle catch 748. This drift may allow the needle 734 to miss the catch 748, causing an incomplete suturing cycle. It is desirable, then, to increase the circumferential length of the needle carrier left inside the guide track in order to improve the guidance of the needle carrier.

Accordingly, the embodiment illustrated in FIGS. 9C and 9D shows the needle carrier 780 with the saddle 784. The saddle 784 allows the flexible carrier driver 782 to exit from the needle carrier 780 at a point along the circumference, rather than at a distal end 804. This may be seen to increase the overall arc length of the needle carrier 780 when compared with the needle carrier 728 shown in FIG. 9A. As a result, when the flexible carrier driver 782 is slidably moved in the guided pathway 774, and the needle carrier 780 is caused to rotate within the needle carrier guide track 776, it may be seen by referring to FIG. 9D that when the bullet needle 786 enters the needle catch 800, a significantly larger portion of the needle carrier 780 is still captured within the needle carrier guide track 776. This may be seen to provide additional guidance to the needle carrier 780 as it penetrates tissue. It may also be seen that the geometry described above allows for a longer stroke length, and therefor greater tissue bite.

Figure 12:
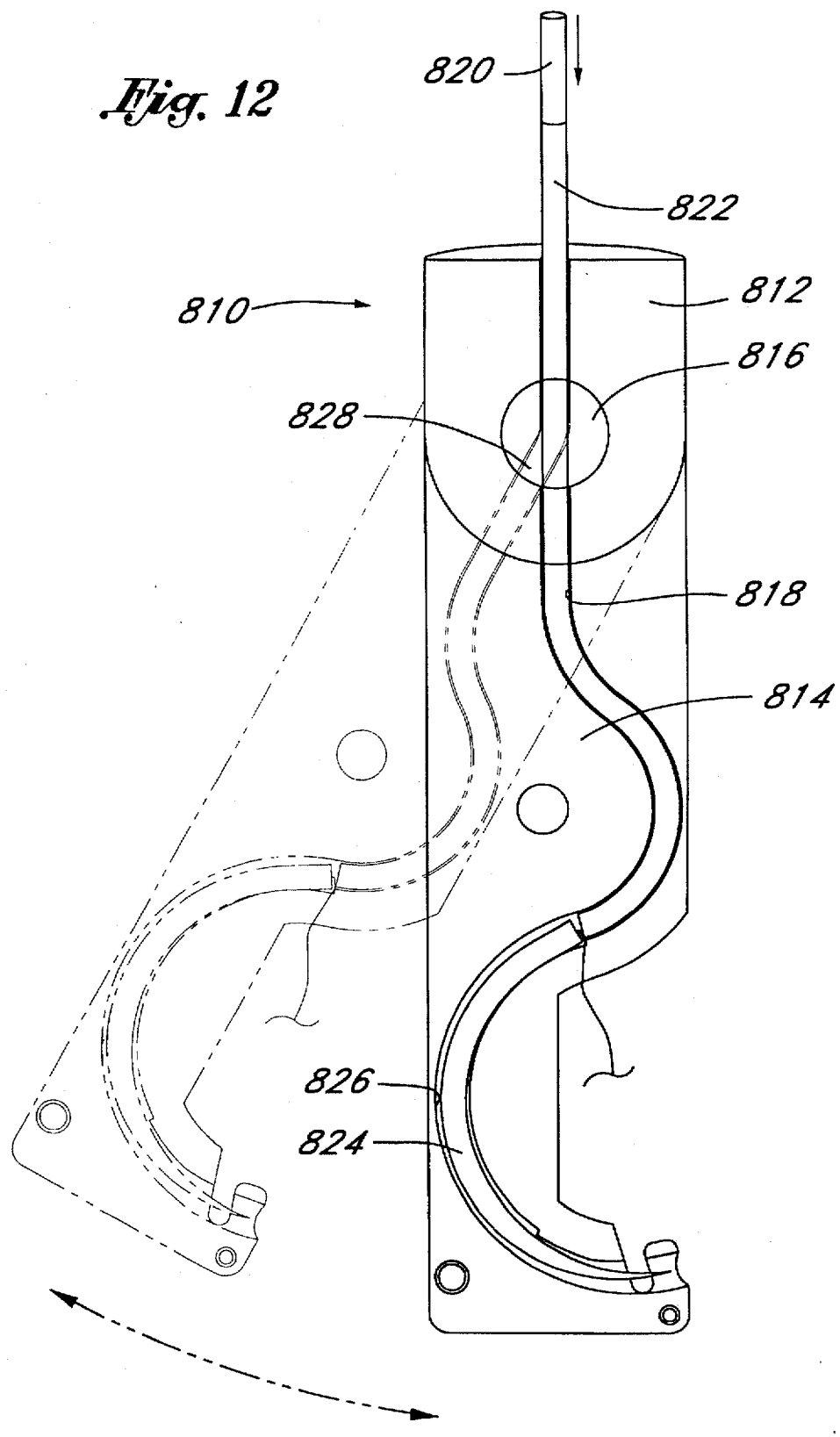
FIG. 12 is a detailed plan view of a modification of a needle delivery system to include an articulating head.

Yet another embodiment of the invention is an alternate needle driver and catch system as shown in FIG. 12, which is detailed cross sectional view of the distal end of a suture application system and is similar in construction to that previously described in FIG. 3. Referring now to FIG. 12, there may be seen a cannular body 810 which includes housing halves 812a,b and articulating tips 814a,b. It is to be understood that for clarity only one of the housing halves 812 and articulating tips 814 of the cannular body 810 is shown in FIG. 12. The housing half 812 is joined to the articulating tip 814 at a pivot 816, and are configured to comprise a continuous pathway 818. A rigid tube 820 is attached to a flexible needle driver 822 in a manner previously described, and is slidably disposed within the continuous pathway 818. A needle 824 is slidably and rotationally disposed within a needle groove 826. The pivot 816 includes an angular opening 828, said angular opening 828 and the needle groove 826 being part of the continuous pathway 818. The articulating tip 814 may be rotated from the initial position shown, about the pivot 816 to the secondary position, with the flexible needle driver 822 being allowed to flex in the angular opening 828, preserving the continuous pathway 818.

The operation of the needle driver portion of this embodiment is substantially the same as that described previously in FIGS. 3 and 5A–5D. The rotation of the articulating tip 814 allows the needle 824 exit angle to be adjusted, as well as to allow the needle 824 to be positioned for access to tissues not directly approachable by a traditional needle driver.

The requirements for the number of times the needle must be passed through tissue depends on the operative procedure being performed by the surgeon. There are times when a running stitch, or uninterrupted suture must be placed, such as for the approximation of tissue flaps during the performance of a Nissen Fundoplication procedure for treatment of gastro-esophageal reflux disorder, or the repair of the uterus after a myomectomy. During these procedures, it may be convenient for the physician to reload the needle intracorporeally, that is, inside the body, in order to pass the needle through the tissue multiple times. Accordingly, we now describe an embodiment of a suture application system which allows the surgeon to reload the needle while the device is inside the body.

Figure 13A:
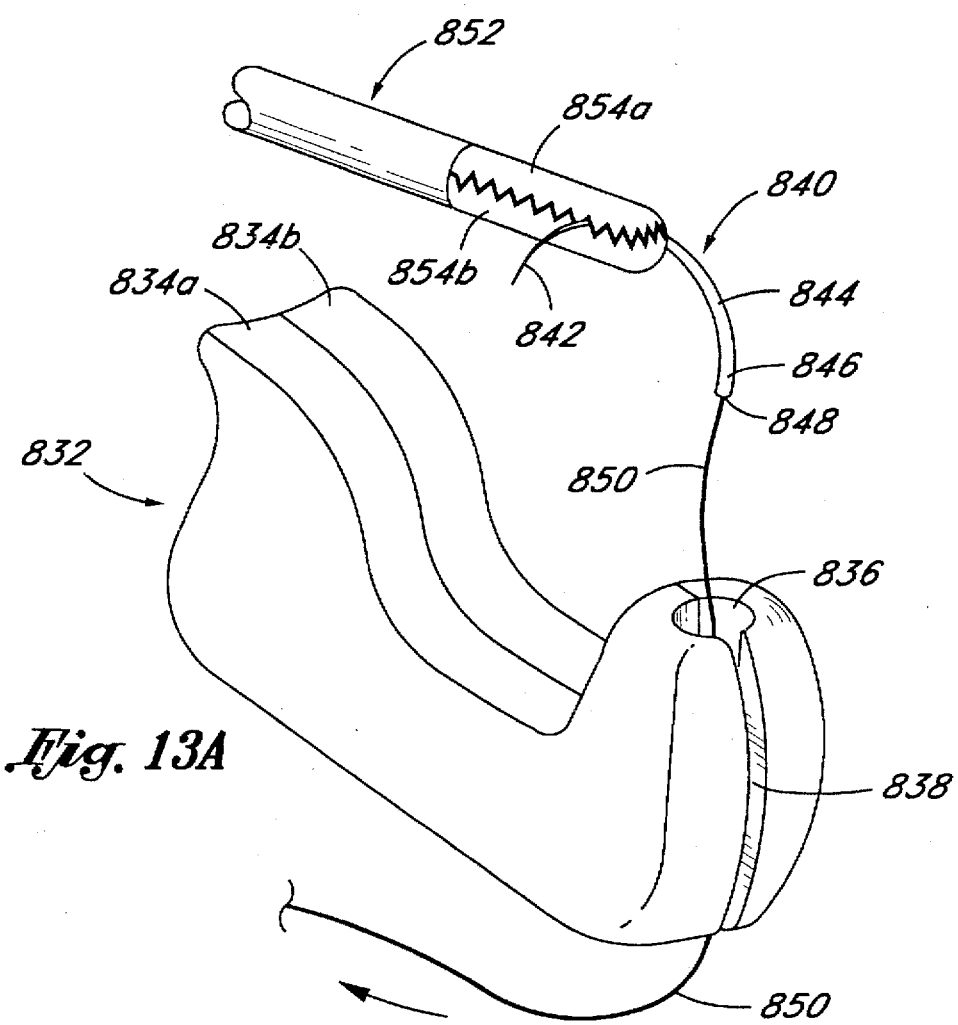
FIGS. 13A and 13B are detailed plan views of the end of a needle delivery system with features adapted for reloading a curved needle intracorporeally, that is, inside the body.
Figure 13B:
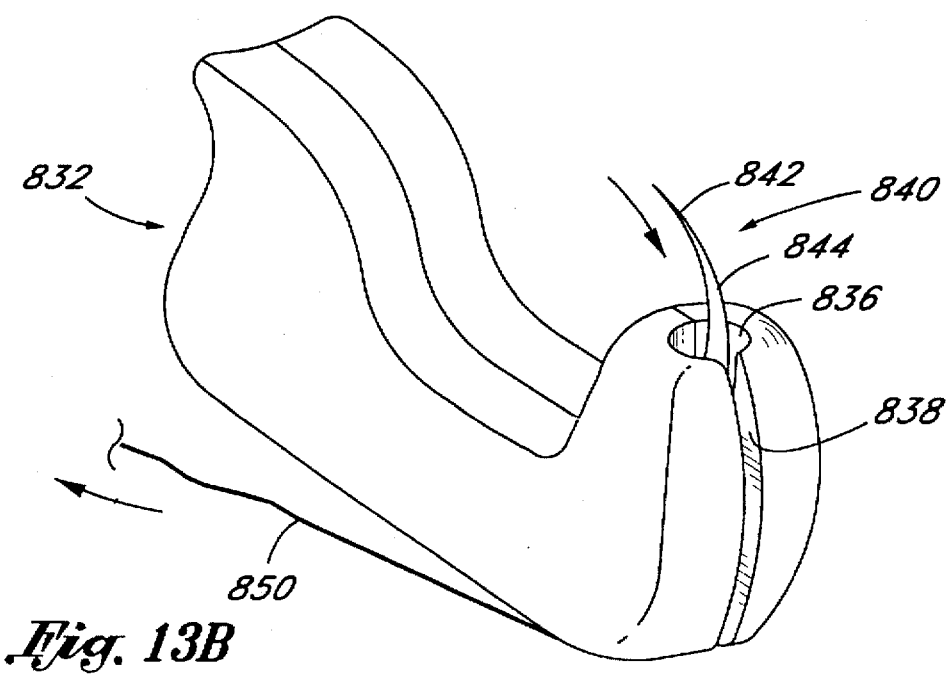

Refer now to FIGS. 13A and 13B where there may be seen detail perspective views of the distal end of a suture application system similar in construction and operation to that described previously in FIGS. 3, 4A and 4B. The suture application system includes a cannular body 832 which is comprised of housing halves 834a,b and includes an opening 836 and a suture slot 838 formed in the housing halves 834a,b. A surgical needle 840 includes a point 842, a needle body 844, and a distal end 846, in which is drilled a hole 848. A suture 850 is crimped, adhesively bonded or otherwise attached to the needle 840 by inserting the suture into the hole 848. A grasper 852 includes jaws 854a,b. It will be understood by those skilled in the art that grasper 852 is a common endoscopic tool used for tissue manipulation or other tasks requiring oppositional pinching. It may also be understood that endoscopic needle holders or the like may be substituted for the graspers illustrated here.

The operation of the needle loading aspects of this embodiment will be described by first referring to FIG. 13A, where the surgical needle 840 is shown being held in the jaws 854 of the grasper 852. The suture 850 is trailing back from the needle 840 to tissue through which it has already been passed. The grasper 852 holding the needle 840 is manipulated to hold the suture 850 in tension while the suture 850 is guided into the suture slot 838. The grasper 852 is opened, releasing the needle 840, and by pulling on the suture 850 in the direction of the arrow as shown in FIG. 13A, the distal end 846 of the needle 840 is pulled into the opening 836 as shown in FIG. 13B. The needle 840 may be completely pulled into the cannular body 832 by continued tension on the suture 850, and prepared for subsequent driving through tissue as previously described in the embodiments above.

It will be understood that the apparatus and method of the present invention for an endoscopic suture system may be employed in numerous specific embodiments in addition to those described herein. Thus, these numerous other embodiments of the invention, which will be obvious to one skilled in the art, including but not limited to changes in the dimensions of the device, the type of materials employed, the location and type of needles, driving mechanisms, catching mechanisms, needle loading mechanisms, etc., are to be included within the scope of the present invention. The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A needle catch made by the process comprising the steps of:

selecting a substantially planar foundation having a first surface and a second surface; and forming at least one aperture in said substantially planar foundation, wherein a first surface lateral dimension of said aperture on said first surface of said foundation is larger than a second surface lateral dimension of said aperture on said second surface of said foundation.

2. A needle catch made by the process defined in claim 1 wherein said step of forming at least one aperture further comprises the step of etching said substantially planar foundation.

3. A needle catch made by the process defined in claim 2 wherein said etching step further comprises the step of etching said substantially planar foundation from only one of said first surface or said second surface.

4. A needle catch made by the process defined in claim 1 wherein said aperture is a flexible aperture.

5. A needle catch comprising:

a substantially planar foundation having a first surface and a second surface; and at least one aperture formed in said substantially planar foundation, wherein a first surface lateral dimension of said aperture on said first surface of said foundation is larger than a second surface lateral dimension of said aperture on said second surface of said foundation.

6. A needle catch as defined by claim 5 wherein said aperture is a flexible aperture.

7. A needle catch as defined by claim 5 further comprising a second aperture positioned adjacent to said at least one aperture wherein said second aperture has a first surface lateral dimension on said first surface of said foundation which is larger than a second surface lateral dimension on said second surface of said foundation.

8. A needle catch made by the process comprising the steps of:

selecting a substantially planar foundation having a first surface and a second surface; and forming a plurality of adjacent flexible apertures in said substantially planar foundation, wherein a first surface lateral dimension of each of said plurality of flexible apertures on said first surface of said foundation is larger than a second surface lateral dimension of each of said plurality of flexible apertures on said second surface of said foundation.

9. A needle catch made by the process defined in claim 8 wherein said step of forming a plurality of adjacent flexible apertures further comprises the step of etching said substantially planar foundation.

10. A needle catch made by the process defined in claim 9 wherein said etching step further comprises the step of etching said substantially planar foundation from only one of said first surface or said second surface.

* * * * *